United States Patent
Oancea

(10) Patent No.: US 11,674,142 B2
(45) Date of Patent: Jun. 13, 2023

(54) METHODS AND COMPOSITIONS FOR TREATING, PREVENTING OR REVERSING OBESITY AND OBESITY-RELATED DISORDERS BY OPSIN 3 REGULATION OF HYPOTHALAMIC MELANOCORTIN RECEPTORS

(71) Applicant: Brown University, Providence, RI (US)

(72) Inventor: Elena Oancea, East Greenwich, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 17/761,975

(22) PCT Filed: Sep. 25, 2020

(86) PCT No.: PCT/US2020/052676
§ 371 (c)(1),
(2) Date: Mar. 18, 2022

(87) PCT Pub. No.: WO2021/062124
PCT Pub. Date: Apr. 1, 2021

(65) Prior Publication Data
US 2022/0389431 A1    Dec. 8, 2022

Related U.S. Application Data

(60) Provisional application No. 62/905,765, filed on Sep. 25, 2019.

(51) Int. Cl.
*C12N 15/113* (2010.01)
*A61P 3/04* (2006.01)

(52) U.S. Cl.
CPC ............ *C12N 15/1138* (2013.01); *A61P 3/04* (2018.01); *C12N 2310/531* (2013.01)

(58) Field of Classification Search
CPC .......... C12N 15/1138; C12N 2310/531; C12N 15/113
See application file for complete search history.

(56) References Cited

U.S. PATENT DOCUMENTS

| | | |
|---|---|---|
| 2007/0203083 A1 | 8/2007 | Mootha et al. |
| 2012/0164148 A1 | 6/2012 | Roesch et al. |
| 2013/0011850 A1 | 1/2013 | Zhang et al. |
| 2013/0096050 A1 | 4/2013 | Shandler |
| 2013/0309254 A1 | 11/2013 | Samuels et al. |
| 2015/0057334 A1 | 2/2015 | Hall et al. |
| 2019/0135926 A1 | 5/2019 | Glanville |

OTHER PUBLICATIONS

Bagnol D et al., "The anatomy of an endogenous antagonist: Relationship between agouti-related protein and proopiomelanocortin in brain", J. Neurosci 1999; 19:RC26.

Begriche K et al., "Genetic Dissection of the Functions of the Melanocortin-3 Receptor, a Seven-transmembrane G-protein-coupled Receptor, Suggests Roles for Central and Peripheral Receptors in Energy Homeostasis", J Biol Chem 2011;286:40771-81.
Blackshaw S et al., "Encephalopsin: A Novel Mammalian Extraretinal Opsin Discretely Localized in the Brain", Journal of Neuroscience 1999; 19:3681-90.
Buhr Ed et al., "Neuropsin (OPN5)-mediated photoentrainment of local circadian oscillators in mammalian retina and cornea", Proc Natl Acad Sci USA 2015; 112:13093-8.
Burke LK et al., "Sex difference in physical activity, energy expenditure and obesity driven by a subpopulation of hypothalamic POMC neurons", Molecular Metabolism 2016; 5:245-52.
Butler AA et al., "A Unique Metabolic Syndrome Causes Obesity in the Melanocortin-3 Receptor-Deficient Mouse", Endocrinology 2000; 141:3518-21.
Chhajlani V. (1996) Distribution of cDNA for melanocortin receptor subtypes in human tissues. Biochemistry & Molecular Biology International, Feb.;38(1): 73-80.
Do Carmo et al., "Role of the brain melanocortins in blood pressure regulation", Biochim Biophys Acta Mol Basis Dis, http://dx.doi.org/10.1016/j.bbadis.2017.03.003, Oct. 2017, pp. 2508-2514.
Ehtesham et al., "Loss-of-function mutations in the melanocortin-3 receptor gene confer risk for human obesity: A systematic review and meta-analysis", Obesity Reviews, DOI: 10.1111/obr.12864, vol. 20, Issue 8, 2019, pp. 1085-1092.
Erola et al., "Hypothalamic γ-melanocyte stimulating hormone gene delivery reduces fat mass in male mice", doi: 10.1530/JOE-18-0009, vol. 239, Issue 1, Oct. 2018, 39 pages.
Fairbrother et al., "Genetics of Severe Obesity", Current Diabetes Reports, vol. 18, Issue 85, https://doi.org/10.1007/s11892-018-1053-x, Aug. 18, 2018, pp. 1-9.
Ghamari-Langroudi M et al., "Regulation of Energy Rheostasis by the Melanocortin-3 Receptor", Science Advances 2018; 4.
Grabinski TM et al., "In Situ Hybridization with Immunohistochemistry in Thick Free-Floating Brain Sections and Primary Neuronal Cultures", Proc Natl Acad Sci USA 2015; 10:e0120120.
Haltaufderhyde K et al., "Opsin expression in human epidermal skin", Photochem Photobiol 2015; 91:117-23.
Hong J et al., "Differential susceptibility to obesity between male, female and ovariectomized female mice", Nutrition Journal 2009; 8:11.

(Continued)

*Primary Examiner* — J. E. Angell
(74) *Attorney, Agent, or Firm* — Adler Pollock & Sheehan P.C.; Michel Morency

(57) ABSTRACT

Described herein are methods and compositions for the prevention or treatment of obesity and obesity-related disorders. The methods and compositions are based, inter alia, on the observations that OPN3 is the most highly expressed opsin in the hypothalamus, a key site for the regulation of energy homeostasis. Indeed, OPN3 expression was highest in regions associated with energy homeostasis, namely the paraventricular nucleus and arcuate nucleus of the hypothalamus. OPN3 was shown to interact and form a complex with MC3R and MC4R, and to modulate MC3R- and MC4R-mediated signaling in the hypothalamus. Accordingly, the methods involve the regulation of melanocortin receptors by downregulating opsin 3 (OPN3) protein expression, OPN3 gene expression, and/or OPN3 activation in the hypothalamus.

4 Claims, 10 Drawing Sheets
Specification includes a Sequence Listing.

(56) References Cited

OTHER PUBLICATIONS

Huszar D et al., "Targeted disruption of the melanocortin-4 receptor results in obesity in mice", Cell 1997; 88:131-141.
International Search Report and Written Opinion received in International Application No. PCT/US2020/052676 dated Mar. 25, 2021, 17 pages.
Koochakpoor et al., "Effect of interactions of polymorphisms in the Melanocortin-4 receptor gene with dietary factors on the risk of obesity and Type 2 diabetes: a systematic review", DIABETICMedicine, DOI: 10.1111/dme.13052, vol. 33, Issue 8, 2015, pp. 1026-1034.
Koyanagi M et al., "Homologs of vertebrate Opn3 potentially serve as a light sensor in nonphotoreceptive tissue", Proc Natl Acad Sci USA 2013; 110:4998-5003.
Lee EJ et al., "Differential regulation of cAMP-mediated gene transcription and ligand selectivity by MC3R and MC4R melanocortin receptors", European Journal of Biochemistry 2001; 268:582.
Lein, E. S. et al., "Genome-wide atlas of gene expression in the adult mouse brain", Nature 2007; 445: 168-176.
Litt et al., "Loss of the melanocortin-4 receptor in mice causes dilated cardiomyopathy", elifesciences.org, DOI: https://doi.org/10.7554/eLife.28118.001, 2017, pp. 1-21.
Liu, H. et al., "Transgenic Mice Expressing Green Fluorescent Protein under the Control of th Melanocortin-4 Receptor Promoter", Journal of Neuroscience 2013; 23: 7143-7154.
Mauvais-Jarvis F., "Sex differences in metabolic homeostasis, diabetes, and obesity", Biology of Sex Differences 2015; 1-9.
Nayak et al., "Adaptive Thermogenesis in Mice is Enhanced by Opsin 3-Dependent Adipocyte Light Sensing", Cell Reports, vol. 30, Issue 3, Jan. 21, 2020, pp. 672-686.
Ortiz et al., "Opsin 3 and 4 Mediate Light-induced Pulmonary Vasorelaxation that is Potentiated by G Protein-coupled Receptor Kinase 2 Inhibition", American Journal of Physiology Lung Cellular and Molecular Physiology, vol. 314, Issue 1, 2018, pp. L93-L106.
Ozdeslik et al., "Human Nonvisual Opsin 3 Regulates Pigmentation of Epidermal Melanocytes Through Functional Interaction with Melanocortin 1 Receptor", Pree Natl Acad Sci US A., vol. 116, Issue 23, May 16, 2019, pp. 1-10.
Regard et al., "Anatomical Profiling of G Protein-coupled Receptor Expression", Cell, vol. 135, Issue 3, Oct. 31, 2008, pp. 561-571.
Roselli-Rehfuss L et al., "Identification of a receptor for gamma melanotropin and other proopiomelanocortin peptides in the hypothalamus and limbic system", Proc Natl Acad Sci USA 2005; 90:8856-60.
Sato et al., "Cell-autonomous Light Sensitivity via Opsin3 Regulates Fuel Utilization in Brown Adipocytes", PLOS Biology 2020, vol. 18, Issue 2, e3000630, Feb. 10, 2020, pp. 1-27.
Sloboda et al., "Fatty Acids Impair Endothelium-Dependent Vasorelaxation: A Link Between Obesity and Arterial Stiffness in Very Old Zucker Rats", Journal of Gerontology: Biological sciences, vol. 67, Issue 9, Sep. 2012, pp. 927-938.
Sugihara T et al., "Absorption Characteristics of Vertebrate Non-Visual Opsin, Opn3", PlosONE2016; 11:e0161215-5.
Van Der Ploeg Lht et al., "Inactivation of the mouse melanocortin-3 receptor results in increased fat mass and reduced lean body mass", Nature Genetics 2000; 26:97-102.
Eerola et al., "Hypothalamic γ-melanocyte stimulating hormone gene delivery reduces fat mass in male mice", doi: 10.1530/JOE-18-0009, vol. 239, Issue 1, Oct. 2018, 39 pages.
Chhajlani, V., "Distribution of cDNA for melanocortin receptor subtypes in human tissues", Biochemistry & Molecular Biology International, vol. 38, No. 1, 1996, pp. 73-80.

Human MCxR Protein Alignment

FIG. 12

```
                       SEQUENCE LISTING

<160> NUMBER OF SEQ ID NOS: 12

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccggcgcatc taaggtcgat gtcatctcga gatgacatcg accttagatg cgttttt       57

<210> SEQ ID NO 2
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccggcattac ctatatctgg ctctactcga gtagagccag atataggtaa tgttttt       57

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccggcgactg agcaagacaa attatctcga gataatttgt cttgctcagt cgttttt       57

<210> SEQ ID NO 4
<211> LENGTH: 202
<212> TYPE: PRT
<213> ORGANISM: Homo sapiens

<400> SEQUENCE: 4

Met Ala Val Gln Gly Ser Gln Arg Arg Leu Leu Gly Ser Leu Asn Ser
1               5                   10                  15
```

```
Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Met Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
130                 135                 140

Ser Ile Phe Tyr Ala Leu Arg Tyr His Ser Ile Val Thr Leu Pro Arg
145                 150                 155                 160

Ala Arg Arg Ala Val Ala Ala Ile Trp Val Ala Ser Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu
            195                 200

<210> SEQ ID NO 5
<211> LENGTH: 85
<212> TYPE: PRT
<213> ORGANISM: Homo sapiens

<400> SEQUENCE: 5

Ala Val Leu Tyr Val His Met Leu Ala Arg Ala Cys Gln His Ala Gln
1               5                   10                  15

Gly Ile Ala Arg Leu His Lys Arg Gln Arg Pro Val His Gln Gly Phe
            20                  25                  30

Gly Leu Lys Gly Ala Val Thr Leu Thr Ile Leu Leu Gly Ile Phe Phe
        35                  40                  45

Leu Cys Trp Gly Pro Phe Phe Leu His Leu Thr Leu Ile Val Leu Cys
50                  55                  60

Pro Glu His Pro Thr Cys Gly Cys Ile Phe Lys Asn Phe Asn Leu Phe
65                  70                  75                  80

Leu Ala Leu Ile Ile
                85

<210> SEQ ID NO 6
<211> LENGTH: 28
<212> TYPE: PRT
<213> ORGANISM: Homo sapiens

<400> SEQUENCE: 6

Asn Ala Ile Ile Asp Pro Leu Ile Tyr Ala Phe His Ser Gln Glu Leu
1               5                   10                  15

Arg Arg Thr Leu Lys Glu Val Leu Thr Cys Ser Trp
            20                  25

<210> SEQ ID NO 7
```

<211> LENGTH: 297
<212> TYPE: PRT
<213> ORGANISM: Homo sapiens

<400> SEQUENCE: 7

Met Lys His Ile Ile Asn Ser Tyr Glu Asn Ile Asn Asn Thr Ala Arg
1               5                   10                  15

Asn Asn Ser Asp Cys Pro Arg Val Val Leu Pro Glu Glu Ile Phe Phe
            20                  25                  30

Thr Ile Ser Ile Val Gly Val Leu Glu Asn Leu Ile Val Leu Leu Ala
        35                  40                  45

Val Phe Lys Asn Lys Asn Leu Gln Ala Pro Met Tyr Phe Phe Ile Cys
50                  55                  60

Ser Leu Ala Ile Ser Asp Met Leu Gly Ser Leu Tyr Lys Ile Leu Glu
65                  70                  75                  80

Asn Ile Leu Ile Ile Leu Arg Asn Met Gly Tyr Leu Lys Pro Arg Gly
                85                  90                  95

Ser Phe Glu Thr Thr Ala Asp Asp Ile Ile Asp Ser Leu Phe Val Leu
            100                 105                 110

Ser Leu Leu Gly Ser Ile Phe Ser Leu Ser Val Ile Ala Ala Asp Arg
        115                 120                 125

Tyr Ile Thr Ile Phe His Ala Leu Arg Tyr His Ser Ile Val Thr Met
130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro Thr Val Ile
                165                 170                 175

Thr Phe Thr Ser Leu Phe Pro Leu Met Leu Val Phe Ile Leu Cys Leu
            180                 185                 190

Tyr Val His Met Phe Leu Leu Ala Arg Ser His Thr Arg Lys Ile Ser
        195                 200                 205

Thr Leu Pro Arg Ala Asn Met Lys Gly Ala Ile Thr Leu Thr Ile Leu
210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
        275                 280                 285

Lys Met Ile Phe Cys Ser Arg Tyr Trp
290                 295

<210> SEQ ID NO 8
<211> LENGTH: 239
<212> TYPE: PRT
<213> ORGANISM: Homo sapiens

<400> SEQUENCE: 8

Met Ser Ile Gln Lys Thr Tyr Leu Glu Gly Asp Phe Val Phe Pro Val
1               5                   10                  15

Ser Ser Ser Ser Phe Leu Arg Thr Leu Leu Glu Pro Gln Leu Gly Ser
            20                  25                  30

Ala Leu Leu Thr Ala Met Asn Ala Ser Cys Cys Leu Pro Ser Val Gln
        35                  40                  45

```
Pro Thr Leu Pro Asn Gly Ser Glu His Leu Gln Ala Pro Phe Phe Ser
    50                  55                  60

Asn Gln Ser Ser Ser Ala Phe Cys Glu Gln Val Phe Ile Lys Pro Glu
 65                  70                  75                  80

Val Phe Leu Ser Leu Gly Ile Val Ser Leu Leu Glu Asn Ile Leu Val
                 85                  90                  95

Ile Leu Ala Val Val Arg Asn Gly Asn Leu His Ser Pro Met Tyr Phe
            100                 105                 110

Phe Leu Cys Ser Leu Ala Val Ala Asp Met Leu Val Ser Val Ser Asn
        115                 120                 125

Ala Leu Glu Thr Ile Met Ile Ala Ile Val His Ser Asp Tyr Leu Thr
    130                 135                 140

Phe Glu Asp Gln Phe Ile Gln His Met Asp Asn Ile Phe Asp Ser Met
145                 150                 155                 160

Ile Cys Ile Ser Leu Val Ala Ser Ile Cys Asn Leu Leu Ala Ile Ala
                165                 170                 175

Val Asp Arg Tyr Val Thr Ile Phe Tyr Ala Leu Arg Tyr His Ser Ile
            180                 185                 190

Met Thr Val Arg Lys Ala Leu Thr Leu Ile Val Ala Ile Trp Val Cys
        195                 200                 205

Cys Gly Val Cys Gly Val Val Phe Ile Val Tyr Ser Glu Ser Lys Met
    210                 215                 220

Val Ile Val Cys Leu Ile Thr Met Phe Phe Ala Met Met Leu Leu
225                 230                 235

<210> SEQ ID NO 9
<211> LENGTH: 86
<212> TYPE: PRT
<213> ORGANISM: Homo sapiens

<400> SEQUENCE: 9

Gly Thr Leu Tyr Val His Met Phe Leu Phe Ala Arg Leu His Val Lys
 1               5                  10                  15

Arg Ile Ala Ala Leu Pro Pro Ala Asp Gly Val Ala Pro Gln Gln His
                20                  25                  30

Ser Cys Met Lys Gly Ala Val Thr Ile Thr Ile Leu Leu Gly Val Phe
            35                  40                  45

Ile Phe Cys Trp Ala Pro Phe Phe Leu His Leu Val Leu Ile Ile Thr
        50                  55                  60

Cys Pro Thr Asn Pro Tyr Cys Ile Cys Tyr Thr Ala His Phe Asn Thr
 65                  70                  75                  80

Tyr Leu Val Leu Ile Met
                85

<210> SEQ ID NO 10
<211> LENGTH: 33
<212> TYPE: PRT
<213> ORGANISM: Homo sapiens

<400> SEQUENCE: 10

Asn Ser Val Ile Asp Pro Leu Ile Tyr Ala Phe Arg Ser Leu Glu Leu
 1               5                  10                  15

Arg Asn Thr Phe Arg Glu Ile Leu Cys Gly Cys Asn Gly Met Asn Leu
                20                  25                  30

Gly
```

```
<210> SEQ ID NO 11
<211> LENGTH: 332
<212> TYPE: PRT
<213> ORGANISM: Homo sapiens

<400> SEQUENCE: 11

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 12
<211> LENGTH: 325
<212> TYPE: PRT
<213> ORGANISM: Homo sapiens

<400> SEQUENCE: 12
```

-continued

```
Met Asn Ser Ser Phe His Leu His Phe Leu Asp Leu Asn Leu Asn Ala
1               5               10              15

Thr Glu Gly Asn Leu Ser Gly Pro Asn Val Lys Asn Lys Ser Ser Pro
            20              25              30

Cys Glu Asp Met Gly Ile Ala Val Glu Val Phe Leu Thr Leu Gly Val
        35              40              45

Ile Ser Leu Leu Glu Asn Ile Leu Val Ile Gly Ala Ile Val Lys Asn
    50              55              60

Lys Asn Leu His Ser Pro Met Tyr Phe Phe Val Cys Ser Leu Ala Val
65              70              75              80

Ala Asp Met Leu Val Ser Met Ser Ser Ala Trp Glu Thr Ile Thr Ile
            85              90              95

Tyr Leu Leu Asn Asn Lys His Leu Val Ile Ala Asp Ala Phe Val Arg
            100             105             110

His Ile Asp Asn Val Phe Asp Ser Met Ile Cys Ile Ser Val Val Ala
        115             120             125

Ser Met Cys Ser Leu Leu Ala Ile Ala Val Asp Arg Tyr Val Thr Ile
        130             135             140

Phe Tyr Ala Leu Arg Tyr His His Ile Met Thr Ala Arg Arg Ser Gly
145             150             155             160

Ala Ile Ile Ala Gly Ile Trp Ala Phe Cys Thr Gly Cys Gly Ile Val
            165             170             175

Phe Ile Leu Tyr Ser Glu Ser Thr Tyr Val Ile Leu Cys Leu Ile Ser
            180             185             190

Met Phe Phe Ala Met Leu Phe Leu Leu Val Ser Leu Tyr Ile His Met
        195             200             205

Phe Leu Leu Ala Arg Thr His Val Lys Arg Ile Ala Ala Leu Pro Gly
210             215             220

Ala Ser Ser Ala Arg Gln Arg Thr Ser Met Gln Gly Ala Val Thr Val
225             230             235             240

Thr Met Leu Leu Gly Val Phe Thr Val Cys Trp Ala Pro Phe Phe Leu
            245             250             255

His Leu Thr Leu Met Leu Ser Cys Pro Gln Asn Leu Tyr Cys Ser Arg
            260             265             270

Phe Met Ser His Phe Asn Met Tyr Leu Ile Leu Ile Met Cys Asn Ser
        275             280             285

Val Met Asp Pro Leu Ile Tyr Ala Phe Arg Ser Gln Glu Met Arg Lys
    290             295             300

Thr Phe Lys Glu Ile Ile Cys Cys Arg Gly Phe Arg Ile Ala Cys Ser
305             310             315             320

Phe Pro Arg Arg Asp
            325
```

METHODS AND COMPOSITIONS FOR TREATING, PREVENTING OR REVERSING OBESITY AND OBESITY-RELATED DISORDERS BY OPSIN 3 REGULATION OF HYPOTHALAMIC MELANOCORTIN RECEPTORS

CROSS REFERENCE TO RELATED APPLICATIONS

This application is a national phase filing under 35 U.S.C. § 371 of International Application No. PCT/US2020/052676 filed Sep. 25, 2020, which claims priority from U.S. Provisional Patent Application No. 62/905,765 filed Sep. 25, 2019, the entire contents of which are incorporated herein by reference.

FIELD OF THE INVENTION

The embodiments of the present invention relate to methods and compositions for treating, preventing or reversing obesity and obesity-related disorders. The methods involve the regulation of melanocortin receptors by downregulating opsin 3 (OPN3) protein expression, OPN3 gene expression, and/or OPN3 activation in the hypothalamus.

SEQUENCE LISTING

The instant application contains a Sequence Listing which has been submitted electronically in ASCII format and is hereby incorporated by reference in its entirety. Said ASCII copy, created on Nov. 6, 2020, is named 405505-606001W0SL.txt and is 15,542 bytes in size.

BACKGROUND OF THE INVENTION

Obesity is a complex disease involving an excessive amount of body fat. It is worldwide health problem that is reaching epidemic proportions. The worldwide prevalence of obesity nearly tripled between 1975 and 2016. In 2016, more than 1.9 billion adults were overweight; of these over 650 million were obese. Moreover, 41 million children under the age of 5 were overweight or obese in 2016.

Obesity disrupts many body systems including glucose and lipid metabolism, circadian rhythms and liver function. It also causes or increases inflammation and oxidative stress. Examples of health and social problems thought to be caused or exacerbated by obesity (obesity related disorders) include coronary heart disease, stroke, obstructive sleep apnea, diabetes mellitus type 2, gout, hyperlipidemia, osteoarthritis, reduced fertility, impaired psychosocial function, reduced physical agility and increased risk of accidents, impaired obstetrical performance, reduced economic performance and discrimination and prejudice. One of the strongest links is with type 2 diabetes. Increases in body fat alter the body's response to insulin, potentially leading to insulin resistance. As a result, obesity has been found to reduce life expectancy.

Methods for managing body weight by dietary restriction and/or by exercise are largely ineffective as few people stick to dietary regimens for a long time, and compliance to regular exercise is equally poor. The result is generally a transient phase of weight loss (or weight stability) followed by a return on the trajectory towards obesity.

Drugs to treat obesity can be divided into three groups: those that reduce food intake or appetite suppressants; those that alter metabolism or block the absorption of fat; and those that increase thermogenesis. Currently, there are only two drugs approved by the FDA for the long-term treatment of obesity: the fat absorption blocker orlistat (XENICAL® and ALLI®) and the appetite suppressant sibutramine (MERIDIA®). These drugs cause serious side effects and only result in modest weight loss.

Accordingly, there is a need for effective methods and compositions for the prevention and treatment of obesity and obesity-related disorders.

BRIEF SUMMARY OF THE INVENTION

The embodiments of the present invention provide methods and compositions for treating, preventing or reversing obesity and obesity-related disorders. The methods involve the regulation of hypothalamic melanocortin receptors by downregulating opsin 3 (OPN3) protein expression, OPN3 gene expression, and/or OPN3 activation. In one embodiment, opsin 3 (OPN3) protein expression, OPN3 gene expression, and/or OPN3 activation is downregulated in the hypothalamus.

In one embodiment, the method for treating, preventing or reversing obesity and obesity-related disorders comprises the step of administering to a subject in need thereof a composition that downregulates opsin 3 (OPN3) protein expression, OPN3 gene expression, and/or OPN3 activation in the hypothalamus of the subject, which results in an upregulation of hypothalamic Melanocortin-3 receptor (MC3R) signaling and/or Melanocortin-4 receptor (MC4R) signaling.

In an alternate embodiment, the method for treating, preventing or reversing obesity and obesity-related disorders comprises the step of administering to a subject in need thereof a composition that downregulates opsin 3 (OPN3) protein expression, OPN3 gene expression, and/or OPN3 activation in the fat tissue, pituitary gland, or other parts of the body of the subject that indirectly signal to the hypothalamus and results in an upregulation of hypothalamic MC3R signaling and/or MC4R signaling.

The composition can comprise an OPN3-targeted shRNA, an OPN3-targeted siRNA, and/or an OPN3-targeted CRISPR/Cas9. In one embodiment, the OPN3-targeted shRNA includes one or more shRNA having the nucleic acid sequence of: SEQ ID NO: 1, SEQ ID NO: 2, SEQ ID NO: 3 or functionally-equivalent thereof.

The obesity-related disorder that can be treated by the methods of the present invention include glucose intolerance, diabetes and metabolic syndrome, which are closely linked to obesity and insulin resistance. The method of the present invention can also prevent obesity-related disorders including coronary heart disease, stroke, obstructive sleep apnea, diabetes mellitus type 2, gout, hyperlipidemia, osteoarthritis, reduced fertility, impaired psychosocial function, reduced physical agility.

Other implementations are also described and recited herein.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings:

FIG. 2A: Melanogenesis in human epidermal melanocytes (HEMs) is controlled by Gas-coupled MC1R. We have shown that OPN3 negatively regulates MC1R by coupling to Gai and antagonizing MC1R-mediated increases in cAMP. FIG. 2Bii: MNT-1 cells expressing OPN3-cMCh or MCh have similar cAMP responses to stimulation with prostaglandin (agonist for the melanocytic Gas-coupled prostaglandin receptor), indicating OPN3 specifically modulates MC1R signaling. FIG. 2Biii: Cells pre-treated with PTX (inhibitor of Gai) and stimulated with aMSH have no significant difference in cAMP responses between those expressing OPN3-cMCh or MCh. FIG. 2Biv: Quantification of the maximal cAMP responses to stimuli in B. Error bars±SEM. *p<0.05.

FIG. 3A: Human OPN3 expression is nearly equivalent in the skin and in the brain. FIG. 3B: Expression of human opsins in the hypothalamus, expressed in Transcripts per Kilobase Million (TPM) as sourced from GTEx. OPN3 is uniquely expressed in the regions where MC1R, MC3R, and MC4R are expressed.

FIG. 6A: A schematic for the generation of an OPN3-mCherry mouse line which expresses OPN3-mCherry under the native OPN3 promoter. FIG. 6B: OPN3 expression in the PVN and ARC of the OPN3-mCherry mouse as immunostained with anti-mCherry. Representative of n=3 mice. Abbreviations: ME: median eminence; 3V: third ventricle.

FIG. 7A: Coimmunoprecipitation of HEK293 cells expressing the indicated OPN3, MC1R, MC3R, or MC4R constructs. When immunoprecipitated (IP) with anti-FLAG and blotted (WB) with anti-HA, bands correspond to a physical interaction between OPN3 and the receptor indicated. FIG. 7B: Coimmunoprecipitation of GT1-7 neurons derived from mouse hypothalamus and expressing the indicated constructs. OPN3 interacted with MC3R and MC4R in this neuronal cell line.

FIG. 8A: mRNA expression of indicated genes. FIG. 8B: OPN3 mRNA levels in mHypoE-39 with shRNA-mediated knockdown of OPN3. shRNA cells had less than 12% of the levels in control shRNA cells. Error bars±SEM.

FIG. 9A: mHypoE-39 cells expressing control scrambled shRNA (CTRL shRNA) or OPN3-targetted shRNA (OPN3 shRNA) were transfected with MC3R-n(HAx3) and EPACH187. The cells with reduced levels of OPN3 (grey) have a larger cAMP response to aMSH compared to CTRL (blue). FIG. 9B: mHypoE-39 cells expressing control scrambled shRNA (CTRL shRNA) or OPN3-targetted shRNA (OPN3 shRNA) were transfected with MC4R-n(HAx3) and EPACH187. The cells with reduced levels of OPN3 (grey) have a larger cAMP response to aMSH compared to CTRL (blue). These data suggest OPN3 negatively regulates aMSH-induced cAMP signaling of both MC3R and MC4R.

FIG. 10A: Mean body weight of female WT (n=2) and OPN3$^{-/-}$ (n=2) mice on a high fat diet (HFD) for 11 weeks, p<0.0001. FIG. 10B: Mean body weight of female WT (n=2) and OPN3$^{-/-}$ (n=1) mice on regular chow diet for 11 weeks, p<0.0001. Insets: Average food intake of OPN3$^{-/-}$ and WT mice on each diet, p>0.05, two-way ANOVA with Sidak's Multiple comparison test. Error bars±SEM.

FIG. 12 provides a human MCxR protein alignment of human MC1R (SEQ ID NOS 4-6, respectively, in order of appearance) (NP 002377.4), MC2R (SEQ ID NO: 7) (NP_001278840.1), MC3R (SEQ ID NOS 8-10, respectively, in order of appearance) (NP_063941.3), MC4R (SEQ ID NO: 11) (NP 005903.2), and MC5R (SEQ ID NO: 12) (NP_005904.1).

DETAILED DESCRIPTION OF THE INVENTION

Figure 1:
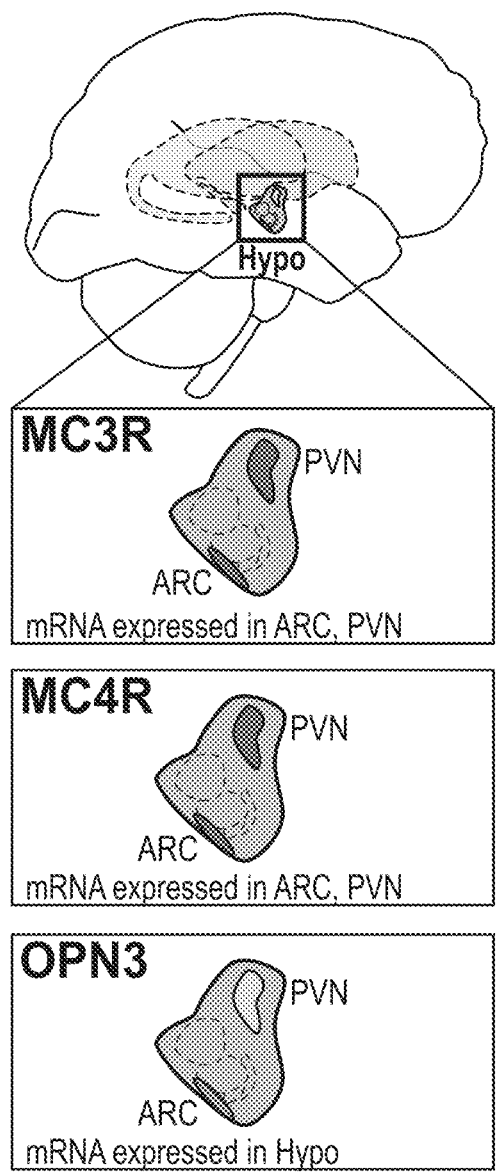
FIG. 1 depicts the distribution of melanocortin-3 receptors (MC3R), melanocortin-4 receptors (MC4R), and opsin 3 (OPN3) in the hypothalamus (Hypo), particularly in the sub-regions: paraventricular nucleus (PVN) and arcuate nucleus (ARC).

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the methods and compositions are described as using specific materials or an order of individual steps, it is appreciated that materials or steps may be interchangeable such that the description of the invention may include multiple parts or steps arranged in many ways as is readily appreciated by one of skill in the art. It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The term "statistically significant" or "significantly" refers to statistical significance and generally means a two standard deviation (2SD) or greater difference.

As used herein, the term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

As used herein, the terms "effective amount" and "therapeutically-effective amount" include an amount sufficient to prevent or ameliorate a manifestation of disease or medical condition, such as obesity, glucose intolerance, diabetes and metabolic syndrome, which are closely linked to obesity and insulin resistance. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treating" or "treatment" or "to treat" or "alleviating" or "to alleviate" refer to both (1) therapeutic measures that cure, slow down, lessen symptoms of, and/or halt progression of a diagnosed disease or infection and (2) prophylactic or preventative measures that prevent or slow the development of a disease or infection.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Antagonist: Those skilled in the art will appreciate that the term "antagonist", as used herein, may be used to refer to an agent (i.e., an "antagonizing agent"), condition, or event whose presence, level, degree, type, or form correlates with decreased level or activity of another agent (i.e., the inhibited agent, or target). In general, an antagonist may be or include an agent of any chemical class including, for example, small molecules, polypeptides, nucleic acids, carbohydrates, lipids, metals, and/or any other entity that shows the relevant inhibitory activity. In some embodiments, an antagonist may be direct (in which case it exerts its influence directly upon its target); in some embodiments, an antagonist may be indirect (in which case it exerts its influence by other than binding to its target; e.g., by interacting with a regulator of the target, so that level or activity of the target is altered). In some embodiments, an antagonist is binding agent that is a protein (e.g., an antibody) or a nucleic acid (e.g., an antisense oligonucleotide) that binds a target (e.g., a protein or nucleic acid) so that the level, form, and/or activity of the target is altered. In some embodiments, the altered level, form and/or activity is a decreased level of altered protein expressed from the target nucleic acid sequence. Those skilled in the art, reading the present disclosure, will appreciate that, in some embodiments, an antagonizing agent may bind to (and potentially antagonize) a binding target, which binding causes a decrease in level or activity of a further antagonized target. To give a specific example, in some embodiments, an antagonizing agent that binds to a nucleic acid target may alter level and/or activity of that target, and in some specific embodiments may antagonize an activity of that nucleic acid target (e.g., by decreasing its modification, splicing, 5' cap formation, and/or 3' end formation, transport, and/or translation, etc., so that a level of an undesired product, e.g., mRNA, is suppressed) and/or may antagonize a downstream target, such as a polypeptide encoded by such nucleic acid target. To give one particular such example, in some embodiment, an antagonizing agent may be or comprise an oligonucleotide that binds to a primary transcript and alters its splicing pattern so that level and/or activity of a particular spliced form (e.g., mature mRNA) is suppressed, which may, in turn achieved decreased level of a product (e.g., a polypeptide) that is or is encoded by such particular spliced form.

Antagonist Therapy: The term "antagonist therapy", as used herein, refers to administration of an antagonist that antagonizes a particular target of interest to achieve a desired therapeutic effect. In some embodiments, antagonist therapy involves administering a single dose of an antagonist. In some embodiments, antagonist therapy involves administering multiple doses of an antagonist. In some embodiments, antagonist therapy involves administering an antagonist according to a dosing regimen known or expected to achieve the therapeutic effect, for example, because such result has been established to a designated degree of statistical confidence, e.g., through administration to a relevant population. In some embodiments, antagonist therapy involves delivery of antagonizing agent as described herein. As noted above, in some embodiments, an antagonizing agent may be or comprise a binding agent that is a protein (e.g., an antibody) or a nucleic acid (e.g., an antisense oligonucleotide) that binds a target (e.g., a protein or nucleic acid) so that level, form, and/or or activity of the target is altered. In some embodiments, an antagonizing agent may bind to (and potentially agonize) a binding target, which binding causes an decrease in level or activity of a further agonized target. To give a specific example, in some embodiments, an antagonizing agent that binds to a nucleic acid target may alter level and/or activity of that target, and in some specific embodiments may antagonize an activity of that nucleic acid target (e.g., by decreasing its modification, splicing, 5' cap formation, and/or 3' end formation, transport, and/or translation, etc., so that a level of a desired product, e.g., mRNA, is generated) and/or may antagonize a downstream target, such as a polypeptide encoded by such nucleic acid target. To give one particular such example, in some embodiment, an antagonizing agent may be or comprise an oligonucleotide that binds to a primary transcript and alters its splicing pattern so that level and/or activity of a particular spliced form (e.g., mature mRNA) is generated, which may, in turn achieved increased level of a product (e.g., a polypeptide) that is or is encoded by such particular spliced form.

Antibody agent: As used herein, the term "antibody agent" refers to an agent that specifically binds to a particular antigen (e.g., that may be or comprise an epitope of a protein of interest, e.g., a OPN3 protein). In some embodiments, the term encompasses any polypeptide or polypeptide complex that includes immunoglobulin structural elements sufficient to confer specific binding. Exemplary antibody agents include, but are not limited to, monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload (e.g., a detectable moiety, a therapeutic moiety, a catalytic moiety, etc.), or other pendant group (e.g., poly-ethylene glycol, etc.). In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody: As used herein, the term "antibody" refers to an immunoglobulin or a derivative thereof containing an immunoglobulin domain capable of binding to an antigen (e.g., that may be or comprise an epitope of a protein of interest, e.g., a MuSK protein). The antibody can be of any species, e.g., human, rodent, rabbit, goat, chicken, etc. The antibody may be a member of any immunoglobulin class, including any of the human classes: IgG, IgM, IgA, IgD, and IgE, or subclasses thereof such as IgG1, IgG2, etc. In various embodiments of the invention the antibody is a fragment such as a Fab', F(ab')$_2$, scFv (single-chain variable) or other fragment that retains an antigen binding site, or a recombinantly produced scFv fragment, including recombinantly produced fragments. See, e.g., Allen, T. (2002), and references therein. The antibody can be monovalent, bivalent or multivalent. The antibody may be a chimeric or "humanized" antibody in which, for example, a variable domain of rodent origin is fused to a constant domain of human origin, thus retaining the specificity of the rodent antibody. The domain of human origin need not originate directly from a human in the sense that it is first synthesized in a human being. Instead, "human" domains may be generated in rodents whose genome incorporates human immunoglobulin genes. See, e.g., Vaughan, et al., (1998). The antibody may be partially or completely humanized. An antibody may be polyclonal or monoclonal, though for purposes of the present invention monoclonal antibodies are generally preferred. Methods for producing antibodies that specifically bind to virtually any molecule of interest are known in the art. For example, monoclonal or polyclonal antibodies can be purified from blood or ascites fluid of an animal that produces the antibody (e.g., following natural exposure to or immunization with the molecule or an antigenic fragment thereof), can be produced using recombinant techniques in cell culture or transgenic organisms, or can be made at least in part by chemical synthesis. In some embodiments, the antibody can act as an antagonist, e.g., by binding to a target antigen, resulting in a decreased level or activity of said antigen. In some embodiments, the antibody can act as an agonist, e.g., by binding to a target antigen, resulting in an increased level or increased activity of said antigen.

Antisense: The term "antisense" is used herein to refer to a nucleic acid whose nucleotide sequence is complementary to part or all of a sequence found in a coding strand nucleic acid. Typically, a "coding strand" nucleic acid is one whose sequence includes part or all of an open reading frame or other stretch of residues that encodes part or all of a polypeptide. In some embodiments, the term "antisense" may particularly be used herein in reference to an oligonucleotide that binds specifically to a coding strand (i.e., to a target sequence within such coding strand). In some embodiments, a coding strand may include both coding and non-coding sequences (e.g., to give but one example, may be a transcript, such as a primary transcript. that includes both intron and exon sequences). Those skilled in the art, reading the present disclosure, will appreciate that, in some embodiments, an oligonucleotide may be considered or referred to as an "antisense" oligonucleotide when some or all of its sequence is complementary to non-coding portion(s) of its target strand. In some embodiments, an antisense oligonucleotide binds to coding sequences in a target sense strand; in some embodiments, an antisense oligonucleotide binds to non-coding sequences in a target coding strand. In some embodiments, an antisense oligonucleotide binds to both coding and non-coding sequences in a target coding strand. In some embodiments, an antisense oligonucleotide is characterized in that, when bound to its target sequence in a coding strand (e.g., a transcript), it alters post-transcriptional processing (e.g., one or more of modification, splicing, 5' cap formation, and/or 3' end formation, 5' cap formation, and/or 3' end formation, transport, and/or translation) of such coding strand. In some particular embodiments, an antisense oligonucleotide alters splicing of its target coding strand. Alternatively or additionally, in some embodiments, an antisense-coding strand complex is or can be degraded, e.g., by RNase H.

Binding agent: In general, the term "binding agent" is used herein to refer to any entity that binds to a target of interest as described herein. In many embodiments, a binding agent of interest is one that binds specifically with its target in that it discriminates its target from other potential binding partners in a particular interaction context. In general, a binding agent may be or comprise an entity of any chemical class (e.g., polymer, non-polymer, small molecule, polypeptide, carbohydrate, lipid, nucleic acid, etc.). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptavidin and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding poiety partner. In some embodiments, binding agents are or comprise polypeptides (including, e.g., antibodies or antibody fragments). In some embodiments, binding agents are or comprise small molecules. In some embodiments, binding agents are or comprise nucleic acids (e.g., antisense oligonucleotides). In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise stapled peptides. In certain embodiments, binding agents are or comprise nucleic acids, such as DNA or RNA (e.g., antisense oligonucleotides).

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Complementary: As used herein, in accordance with its art-accepted meaning, "complementary" refers to the capacity for precise pairing between particular bases, nucleosides, nucleotides or nucleic acids. For example, adenine (A) and uridine (U) are complementary; adenine (A) and thymidine (T) are complementary; and guanine (G) and cytosine (C), are complementary and are referred to in the art as Watson-Crick base pairings. If a nucleotide at a certain position of a first nucleic acid sequence is complementary to a nucleotide located opposite in a second nucleic acid sequence when the strands are aligned in anti-parallel orientation, the nucleotides (nt) form a complementary base pair, and the nucleic acids are complementary at that position. The percent complementarity of a first nucleic acid to a second nucleic acid may be evaluated by aligning them in antiparallel orientation for maximum complementarity over a window of evaluation, determining the total number of nt in both strands that form complementary base pairs within the window, dividing by the total number of nt within the window, and multiplying by 100. For example, AAAAAAAA and TTTGTTAT are 75% complementary since there are 12 nt in complementary base pairs out of a total of 16 nt. When computing the number of complementary nt needed to achieve a particular % complementarity, fractions are rounded to the nearest whole number. A position occupied by non-complementary nucleotides constitutes a mismatch, i.e., the position is occupied by a non-complementary base pair. In certain embodiments a window of evaluation has the length described herein for duplex portions or target portions. Complementary sequences include base-pairing of a polynucleotide comprising a first nucleotide sequence to a polynucleotide comprising a second nucleotide sequence over the entire length of both nucleotide sequences (if the same length) or over the entire length of the shorter sequence (if different lengths). Such sequences can be referred to as "perfectly complementary" (100% complementarity) with respect to each other herein. Nucleic acids that are at least 70% complementary over a window of evaluation are considered "substantially complementary" over that window. In certain embodiments complementary nucleic acids are at least 75%, at least 80%, at least 85%, at least 90%, or at least 95% complementary over the window of evaluation. Where a first sequence is referred to as "substantially complementary" with respect to a second sequence herein, the two sequences may be perfectly complementary or they may comprise one or more unmatched bases upon hybridization, e.g., up to about 5%, 10%, 15%, 20%, or 25% unmatched bases upon hybridization, e.g., 1, 2, 3, 4, 5, or 6 mismatched base pairs upon hybridization for a duplex up to 30 base pairs, while retaining the ability to hybridize under the conditions most relevant to their intended use. It should be understood that where two oligonucleotides are designed to form, upon hybridization, one or more single stranded overhangs, such overhangs are not regarded as mismatches or unpaired nucleotides with regard to the determination of percent complementarity. For example, the two strands of a dsRNA comprising one oligonucleotide 21 nucleotides in length and another oligonucleotide 23 nucleotides in length, wherein the longer oligonucleotide comprises a sequence of 21 nucleotides that is perfectly complementary to the shorter oligonucleotide and a 2 nucleotide overhang, may be referred to as "perfectly complementary" herein. "Complementary" sequences, as used herein may include one or more non-Watson-Crick base pairs and/or base pairs formed from non-natural and other modified nucleotides, in so far as the requirements with respect to their ability to hybridize are fulfilled. Such non-Watson-Crick base pairs include, but are not limited to, G:U Wobble or Hoogsteen base pairing. Those of ordinary skill in the art are aware that guanine, cytosine, adenine, and uracil can be replaced by other bases without substantially altering the base pairing properties of a polynucleotide comprising a nucleotide bearing such bases, according to the so-called "wobble" rules (see, e.g., Murphy & Ramakrishnan (2004). For example, a nucleotide comprising inosine as its base can base pair with nucleotides containing adenine, cytosine, or uracil. Thus, nucleotides containing uracil, guanine, or adenine can be replaced in the nucleotide sequences of an Inhibitory RNA described herein by a nucleotide containing, for example, inosine. It will be understood that the terms "complementary", "perfectly complementary", and "substantially complementary" can be used with respect to the base matching between any two nucleic acids, e.g., the base matching between the sense strand and the antisense strand of a double stranded nucleic acid, or portion thereof. "Hybridize", as used herein, refers to the interaction between two nucleic acid sequences (which in some embodiments may be part of the same nucleic acid molecule and in other embodiments may be or include part(s) of different nucleic acid molecules) comprising or consisting of complementary portions such that a duplex structure (i.e., an intramolecular or intermolecular duplex) is formed that is stable under the particular conditions of interest, as will be understood by the ordinary skilled artisan.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide (e.g., the Ig3 domain of a MuSK protein); in some such embodiments, a domain is characterized by a particular structural element (e.g., a particular amino acid sequence or sequence motif, a-helix character, b-sheet character, coiled-coil character, random coil character, etc.), and/or by a particular functional feature (e.g., binding activity, enzymatic activity, folding activity, signaling activity, etc.).

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) transport of an RNA transcript (e.g., from nucleus to cytoplasm; and/or (4) translation of an RNA into a polypeptide or protein; and/or (4) post-translational modification of a polypeptide or protein.

Fragment: A "fragment" of a material or entity as described herein has a structure that includes a discrete portion of the whole but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the fragment.

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequences. In some embodiments, a gene may include one or more regulatory elements that, for example, may control or impact one or more aspects of gene expression (e.g., cell-type-specific expression, inducible expression, etc.).

Gene product or expression product: As used herein, the term "gene product" or "expression product" generally refers to an RNA transcribed from the gene (pre-and/or post-processing) or a polypeptide (pre- and/or post-modification) encoded by an RNA transcribed from the gene. In some embodiments, a gene product may be or comprise a particular processed form of an RNA transcript (e.g., a particular edited form, a particular splice form, a particular capped form, etc.).

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (1989), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual, a single cell, or cell population) under otherwise comparable conditions absent presence of (e.g., prior to and/or after) a particular agent or treatment, or in presence of an appropriate reference agent (e.g., a positive control agent or a negative control agent). In some embodiments, an appropriate reference measurement may be or comprise a measurement in comparable system known or expected to respond in a particular way, in presence of the relevant agent or treatment. Those skilled in the art will appreciate that an "improvement", "increase", "reduction", etc. typically refers to a statistically significant change. Moreover, those skilled in the art will understand from context what magnitude of change may be relevant. For example, in some embodiments, a change may be a "fold" change, i.e., so that a "changed" value represents a 1.1, 1.2, 2, 3, 4, 5, 6, 7, 8, 9, 10, 15, 20, 30, 40, 50 or more (e.g., 500, 1000 times) (including all integers and decimal points in between and above 1), e.g., 1.5, 1.6, 1.7. 1.8, etc.)-fold difference relative to the relevant reference. Alternatively or additionally, in some embodiments, a "change" may be a "percentage" change, so that a "changed" value represents al %, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase or decrease, including all integers and decimal points in between), relative to the relevant reference.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, 5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide. In some embodiments, a nucleic acid has enzymatic activity.

Prodrug: A general, a "prodrug," as that term is used herein and as is understood in the art, is an entity that, when administered to an organism, is metabolized in the body to deliver an active (e.g., therapeutic or diagnostic) agent of interest. Typically, such metabolism involves removal of at least one "prodrug moiety" so that the active agent is formed. Various forms of "prodrugs" are known in the art. For examples of such prodrug moieties, see:

a) Design of Prodrugs, edited by H. Bundgaard, (Elsevier, 1985) and Methods in Enzymology, 42:309-396, edited by K. Widder, et al., (Academic Press, 1985);
b) Prodrugs and Targeted Delivery, edited by J. Rautio (Wiley, 2011);
c) A Textbook of Drug Design and Development, edited by Krogsgaard-Larsen;
d) Bundgaard, Chapter 5 "Design and Application of Prodrugs", by H. Bundgaard, p. 113-191 (1991);
e) Bundgaard, Advanced Drug Delivery Reviews, 8:1-38 (1992);
f) Bundgaard, et al., Journal of Pharmaceutical Sciences, 77:285 (1988); and
g) Kakeya, et al., Chem. Pharm. Bull., 32:692 (1984).

As with other compounds described herein, prodrugs may be provided in any of a variety of forms, e.g., crystal forms, salt forms etc. In some embodiments, prodrugs are provided as pharmaceutically-acceptable salts thereof.

Patient: As used herein, the term "patient" refers to any organism to which a provided composition (e.g., an agonizing agent such as an ASO) is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is obesity or an obesity-related disorder such as glucose intolerance, diabetes and metabolic syndrome or other disease requiring OPN3 downregulation. In some embodiments, the patient is receiving or has received certain therapy to diagnose and/or to treat a disease, disorder, or condition.

Pharmaceutical Compositions: The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well known in the art. For example, Berge, et al., (1977) describes pharmaceutically-acceptable salts in detail. In some embodiments, pharmaceutically-acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically-acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, a provided compound comprises one or more acidic groups, e.g., an oligonucleotide, and a pharmaceutically-acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically-acceptable salt is a sodium salt. In some embodiments, a pharmaceutically-acceptable salt is a potassium salt. In some embodiments, a pharmaceutically-acceptable salt is a calcium salt. In some embodiments, pharmaceutically-acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, an oligonucleotide may comprise two or more acidic groups (e.g., in natural phosphate linkages and/or modified internucleotidic linkages). In some embodiments, a pharmaceutically-acceptable salt, or generally a salt, of such a compound comprises two or more cations, which can be the same or different. In some embodiments, in a pharmaceutically-acceptable salt (or generally, a salt), all ionizable hydrogen (e.g., in an aqueous solution with a pKa no more than about 11, 10, 9, 8, 7, 6, 5, 4, 3, or 2; in some embodiments, no more than about 7; in some embodiments, no more than about 6; in some embodiments, no more than about 5; in some embodiments, no more than about 4; in some embodiments, no more than about 3) in the acidic groups are replaced with cations. In some embodiments, each internucleotidic linkage, e.g., phosphate group, independently exists in its salt form (e.g., if sodium salt, —O—P(O)(ONa)—O—). In some embodiments, a pharmaceutically-acceptable salt is a sodium salt of an oligonucleotide. In some embodiments, a pharmaceutically-acceptable salt is a sodium salt of an oligonucleotide, wherein each acidic phosphate and modified phosphate group, if any, exists as a salt form (all sodium salt).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragées, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropyl methyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragées, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropyl methyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, micro-emulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically-acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art.[1]

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In other embodiments, the active compound will be administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone or conjointly administered with another type of therapeutic agent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Polypeptide: As used herein, the term "polypeptide," which is interchangeably used herein with the term "protein," refers to a polymer of at least three amino acid residues. In some embodiments, a polypeptide comprises one or more, or all, natural amino acids. In some embodiments, a polypeptide comprises one or more, or all non-natural amino acids. In some embodiments, a polypeptide comprises one or more, or all, D-amino acids. In some embodiments, a polypeptide comprises one or more, or all, L-amino acids. In some embodiments, a polypeptide comprises one or more pendant groups or other modifications, e.g., modifying or attached to one or more amino acid side chains, at the polypeptide's N-terminus, at the polypeptide's C-terminus, or any combination thereof. In some embodiments, a polypeptide comprises one or more modifications such as acetylation, amidation, aminoethylation, biotinylation, carbamylation, carbonylation, citrullination, deamidation, deimination, eliminylation, glycosylation, lipidation, methylation, pegylation, phosphorylation, sumoylation, or combinations thereof. In some embodiments, a polypeptide may participate in one or more intra- or intermolecular disulfide bonds. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may comprise a stapled polypeptide. In some embodiments, a polypeptide participates in non-covalent complex formation by non-covalent or covalent association with one or more other polypeptides (e.g., as in an antibody). In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise a fragment of a parent polypeptide. In some embodiments, a useful polypeptide as may comprise a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or prevention: As used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Recombinant: As used herein, the term "recombinant" is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

RNA Interference (RNAi): As used herein RNAi is a biological process where RNA molecules are used to inhibit gene expression. Typically, short RNA molecules are created that are complementary to endogenous mRNA and when introduced into cells, bind to the target mRNA. Binding of the short RNA molecule to the target mRNA functionally inactivates the target mRNA and sometimes leads to degradation of the target mRNA.

Historically, two types of short RNA molecules have been used in RNAi applications. Small interfering RNA (siRNA) are typically double-stranded RNA molecules, 20-25 nucleotides in length. When transfected into cells, siRNA inhibit the target mRNA transiently until they are also degraded within the cell. Small hairpin RNAs (shRNA) are sequences of RNA, typically about 80 base pairs in length, that include a region of internal hybridization that creates a hairpin structure. shRNA molecules are processed within the cell to form siRNA which in turn knock down gene expression. The benefit of shRNA is that they can be incorporated into plasmid vectors and integrated into genomic DNA for longer-term or stable expression, and thus longer knockdown of the target mRNA.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 Daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not and/or does not comprise a protein or polypeptide (e.g., is not an oligopeptide or peptide). In some embodiments, a small molecule is not and/or does not comprise a polynucleotide (e.g., is not an oligonucleotide). In some embodiments, a small molecule is not and/or does not comprise a polysaccharide; for example, in some embodiments, a small molecule is not a glycoprotein, proteoglycan, glycolipid, etc.). In some embodiments, a small molecule is not a lipid. In some embodiments, a small molecule is a modulating agent (e.g., is an inhibiting agent or an activating agent). In some embodiments, a small molecule is biologically active. In some embodiments, a small molecule is detectable (e.g., comprises at least one detectable moiety). In some embodiments, a small molecule is a therapeutic agent. Those of ordinary skill in the art, reading the present disclosure, will appreciate that certain small molecule compounds described herein may be provided and/or utilized in any of a variety of forms such as, for example, crystal forms, salt forms, protected forms, prodrug forms, ester forms, isomeric forms (e.g., optical and/or structural isomers), isotopic forms, etc. Those of skill in the art will appreciate that certain small molecule compounds have structures that can exist in one or more stereoisomeric forms. In some embodiments, such a small molecule may be utilized in accordance with the present disclosure in the form of an individual enantiomer, diastereomer or geometric isomer, or may be in the form of a mixture of stereoisomers; in some embodiments, such a small molecule may be utilized in accordance with the present disclosure in a racemic mixture form. Those of skill in the art will appreciate that certain small molecule compounds have structures that can exist in one or more tautomeric forms. In some embodiments, such a small molecule may be utilized in accordance with the present disclosure in the form of an individual tautomer, or in a form that interconverts between tautomeric forms. Those of skill in the art will appreciate that certain small molecule compounds have structures that permit isotopic substitution (e.g., $^2$H or $^3$H for H; $^{11}$C, $^{13}$C or $^{14}$C for $^{12}$C; $^{13}$N or $^{15}$N for $^{14}$N; $^{17}$O or $^{18}$O for $^{16}$O; $^{36}$Cl for $^{35}$C; $^{18}$F for $^{131}$I or $^{125}$I for $^{127}$I; etc.). In some embodiments, such a small molecule may be utilized in accordance with the present disclosure in one or more isotopically modified forms, or mixtures thereof. In some embodiments, reference to a particular small molecule compound may relate to a specific form of that compound. In some embodiments, a particular small molecule compound may be provided and/or utilized in a salt form (e.g., in an acid-addition or base-addition salt form, depending on the compound); in some such embodiments, the salt form may be a pharmaceutically-acceptable salt form. In some embodiments, where a small molecule compound is one that exists or is found in nature, that compound may be provided and/or utilized in accordance in the present disclosure in a form different from that in which it exists or is found in nature. Those of ordinary skill in the art will appreciate that, in some embodiments, a preparation of a particular small molecule compound that contains an absolute or relative amount of the compound, or of a particular form thereof, that is different from the absolute or relative (with respect to another component of the preparation including, for example, another form of the compound) amount of the compound or form that is present in a reference preparation of interest (e.g., in a primary sample from a source of interest such as a biological or environmental source) is distinct from the compound as it exists in the reference preparation or source. Thus, in some embodiments, for example, a preparation of a single stereoisomer of a small molecule compound may be considered to be a different form of the compound than a racemic mixture of the compound; a particular salt of a small molecule compound may be considered to be a different form from another salt form of the compound; a preparation that contains only a form of the compound that contains one conformational isomer ((Z) or (E)) of a double bond may be considered to be a different form of the compound from one that contains the other conformational isomer ((E) or (Z)) of the double bond; a preparation in which one or more atoms is a different isotope than is present in a reference preparation may be considered to be a different form; etc.

Specific binding: As used herein, the term "specific binding" refers to an ability to discriminate between possible binding partners in the environment in which binding is to occur. A binding agent that interacts with one particular target when other potential targets are present is said to "bind specifically" to the target (e.g., a target amino acid or nucleic acid sequence on a target protein/gene of interest) with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Specificity: As is known in the art, "specificity" is a measure of the ability of a particular ligand to distinguish its binding partner from other potential binding partners.

Subject: As used herein, the term "subject" refers an organism, typically a mammal (e.g., a human, in some embodiments including prenatal human forms). In some embodiments, a subject is suffering from a relevant disease, disorder or condition (e.g., obesity or an obesity-related disorder such as glucose intolerance, diabetes and metabolic syndrome or other disease requiring OPN3 downregulation). In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial identity: As used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., Basic local alignment search tool, J. Mol. Biol., 215(3): 403-410, 1990; Altschul et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition (e.g., obesity or an obesity-related disorder such as glucose intolerance, diabetes and metabolic syndrome or other disease requiring OPN3 downregulation) has been diagnosed with and/or displays one or more symptoms of a disease, disorder, and/or condition.

Susceptible to: An individual who is "susceptible to" a disease, disorder, and/or condition (e.g., obesity or an obesity-related disorder such as glucose intolerance, diabetes and metabolic syndrome or other disease requiring OPN3 downregulation) is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Symptoms are reduced: According to the present invention, "symptoms are reduced" when one or more symptoms of a particular disease, disorder or condition (e.g., obesity or an obesity-related disorder such as glucose intolerance, diabetes and metabolic syndrome or other disease requiring OPN3 downregulation) is reduced in magnitude (e.g., intensity, severity, etc.) and/or frequency. For purposes of clarity, a delay in the onset of a particular symptom is considered one form of reducing the frequency of that symptom.

Target gene: A "target gene", as used herein, refers to a gene whose expression is to be modulated, e.g., through modifying splice activity (e.g., by inducing exon-skipping). As used herein, the term "target portion" or "target region" refers to a contiguous portion of the nucleotide sequence of a target gene. In some embodiments, a target portion or target region is one or more exons within the target gene sequence. A target portion may be from about 8-36 nucleotides in length, e.g., about 10-20 or about 15-30 nucleotides in length. A target portion length may have specific value or subrange within the afore-mentioned ranges. For example, in certain embodiments a target portion may be between about 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition (e.g., one or more symptoms or features of obesity or an obesity-related disorder such as glucose intolerance, diabetes and metabolic syndrome or other disease requiring OPN3 downregulation).

Therapeutically effective amount: As used herein, the term "therapeutically effective amount" means an amount of a substance (e.g., a therapeutic agent, composition, and/or formulation) that elicits a desired biological response when administered as part of a therapeutic dosing regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition (e.g., one or more symptoms or features of obesity or an obesity-related disorder such as glucose intolerance, diabetes and metabolic syndrome or other disease requiring OPN3 downregulation). In some embodiments, a therapeutically effective amount is administered in a single dose; in some embodiments, multiple unit doses are required to deliver a therapeutically effective amount.

Treating: As used herein, the term "treating" refers to providing treatment, i.e., providing any type of medical or surgical management of a subject. The treatment can be provided in order to reverse, alleviate, inhibit the progression of, prevent or reduce the likelihood of a disease, disorder, or condition, or in order to reverse, alleviate, inhibit or prevent the progression of, prevent or reduce the likelihood of one or more symptoms or manifestations of a disease, disorder or condition. Treating can include administering an agent to the subject following the development of one or more symptoms or manifestations indicative of obesity or an obesity-related disorder such as glucose intolerance, diabetes and metabolic syndrome or other disease requiring OPN3 downregulation, e.g., in order to reverse, alleviate, reduce the severity of, and/or inhibit or prevent the progression of the condition and/or to reverse, alleviate, reduce the severity of, and/or inhibit or one or more symptoms or manifestations of the condition. A composition of the disclosure can be administered to a subject who has developed obesity or an obesity-related disorder such as glucose intolerance, diabetes and metabolic syndrome or other disease requiring OPN3 downregulation or is at increased risk of developing such a disorder relative to a member of the general population. A composition of the disclosure can be administered prophylactically, i.e., before development of any symptom or manifestation of the condition. Typically in this case the subject will be at risk of developing the condition.

Variant: As used herein in the context of molecules, e.g., nucleic acids (e.g., antisense oligonucleotides (ASOs)), proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a "variant" of a reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid comprises about 10, about 9, about 8, about 7, about 6, about 5, about 4, about 3, about 2, or about 1 substituted residues as compared to a reference. Often, a variant polypeptide or nucleic acid comprises a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid comprises not more than about 5, about 4, about 3, about 2, or about 1 addition or deletion, and, in some embodiments, comprises no additions or deletions, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a reference polypeptide or nucleic acid is one found in nature. In some embodiments, a reference polypeptide or nucleic acid is a human polypeptide or nucleic acid.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors". Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., MOLECULAR CLONING: A LABORATORY MANUAL (2012).

OPN3 Antagonizing Agents

The therapeutic agents useful in the method of preventing, treating, or reversing obesity or an obesity-related disorder of the present invention include OPN3 antagonizing agents that downregulate opsin 3 (OPN3) protein expression, OPN3 gene expression, and/or OPN3 activation. The antagonist therapy consists of the administration of one or more OPN3 antagonizing agents, which include, but are not limited to, an anti-OPN3 antibody, a nucleic acid OPN3 antagonizing agent that may be or comprise an oligonucleotide, such as a OPN3-targeted exon-skipping oligonucleotide, an OPN3-targeted CRISPR/Cas9 gRNA (e.g., that modifies and/or removes OPN3), an OPN3 targeted small interfering RNA (siRNA) (e.g., that inhibits production/expression of OPN3, for example from a transcript that encodes it), and/or an OPN3-targeted small hairpin RNA (shRNA) (e.g., that are processed within the cell to form siRNA which in turn knock down OPN3 gene expression).

Several OPN3 antagonizing agents are available commercially. For example, commercially-available anti-OPN3 antibodies include, but are not limited to, Catalog Nos. ABIN350681 and ABIN2139897 (antibodies-online.com); ab75285 (Abcam plc, Cambridge, UK); 144-63924-50 (RayBiotech, Peachtree Corners, Ga.); TA342739 and TA315260 (OriGene Global, Rockville, Md.); 171066 and 171067 (United States Biological, Salem, Mass.); SAB2700986 (Millipore Sigma, Burlington, Mass.); GTX70607 and GTX108155 (GeneTex Inc., Irvine, Calif.); and CABT-BL2786 and CABT-BL2787 (Creative Diagnostics, Shirley, N.Y.).

Commercially-available OPN3 siRNAs include, but are not limited to, Catalog Nos. AM16708, 1299001, 1330001, 4392420, and 4390771 (ThermoFisher Scientific, Waltham, Mass.); SR308392 and SR413372 (OriGene Global, Rockville, Md.); sc-45989 (Santa Cruz Biotechnology, Inc., Santa Cruz, Calif.); MBS8201184 and MBS8203817 (MYBioSource.com); and abx926969 (Abbexa Ltd, Cambridge, UK).

Commercially-available OPN3 shRNAs include, but are not limited to, Catalog Nos. Locus ID 23596 (AMSBIO, Abingdon, UK); TR311018 (ZAGENO Cambridge, Mass.); and TRCN0000028305, TRCN0000028313, TRCN0000028389 (Millipore Sigma, Burlington, Mass.).

Commercially-available OPN3 CRISPR Knockout Vector include, but are not limited to, Catalog No. 3484911 (Applied Biological Materials Inc., Richmond, BC Canada).

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology and molecular biology can be found in THE MERCK MANUAL OF DIAGNOSIS AND THERAPY;[2] THE ENCYCLOPEDIA OF MOLECULAR CELL BIOLOGY AND MOLECULAR MEDICINE;[3] MOLECULAR BIOLOGY AND BIOTECHNOLOGY: A COMPREHENSIVE DESK REFERENCE;[4] IMMUNOLOGY;[5] JANEWAY'S IMMUNOBIOLOGY;[6] LEWIN'S GENES XI;[7] MOLECULAR CLONING: A LABORATORY MANUAL;[5] BASIC METHODS IN MOLECULAR BIOLOGY;[9] LABORATORY METHODS IN ENZYMOLOGY;[10] CURRENT PROTOCOLS IN MOLECULAR BIOLOGY (CPMB);[11] CURRENT PROTOCOLS IN PROTEIN SCIENCE (CPPS);[12] and CURRENT PROTOCOLS IN IMMUNOLOGY (CPI).[13]

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention and are not intended to limit the invention.

Example 1

Materials and Methods

Cell Culture and Transfection

All cell culture reagents were purchased from ThermoFisher Scientific, unless otherwise stated. HeLa cells were maintained under standard conditions in DMEM supplemented with 5% FBS and 100 units/mL penicillin/streptomycin. HeLa cells were transiently transfected using Lipofectamine 2000 according to manufacturer's recommendations. MNT-1 cells were maintained under standard conditions in DMEM supplemented with 18% FBS, 10% AIM-V and 100 units/mL penicillin/streptomycin. MNT-1 cells were transiently transfected with OPN3-cMCh or MCh using Nucleofector™ Kits for Human Melanocytes (Lonza) or using magnetofection with PolyMag Neo magnetic beads (OZ Biosciences) according to manufacturer's instructions. MNT-1 cells stably expressing OPN3-cMCh or MCh were selected for a minimum of 14 days. Normal primary neonatal human epidermal melanocytes (HEMs) were purchased and maintained under standard conditions in Medium 254 supplemented with human melanocyte growth supplement (HMGS-2) and 100 units/mL penicillin and streptomycin. For miRNA experiments, HEMs were transduced with either OPN3-targeted or scrambled miRNAs using BLOCK-IT™ Lentiviral RNAi expression system according to manufacturer's protocol. The lentiviral transduction rates were ~60% as detected by co-expression of MCherry. HEMs expressing miRNAs were selected with blasticidin (4 µg/mL) for at least 14 days.

DNA Constructs cDNA encoding full length human OPN3 was obtained by RT-PCR using RNA extracted from HEMs. OPN3 and different OPN3 variants were cloned into pcDNA4/TO expression vector (Life Technologies). Mutations were introduced by site-directed mutagenesis using the QuickChange® Site-Directed Mutagenesis Kit (Stratagene). The human MC1R-n(3xHA) and EP2-n(3xHA) expression vectors were purchased from www.cDNA.org. All constructs were confirmed by sequencing.

Immunoprecipitation and Western Blot

Cells plated on tissue culture dishes (100 mm) were rinsed with cold PBS before the addition of 500 µL lysis buffer [300 mM NaCl, 50 mM Tris-HCl (pH 7.4), 1% Triton X-100, and protease inhibitor mix (Roche)]. Cells were scraped and homogenized using a 22G syringe needle. Lysates were rotated end-over-end for 1 hour at 4° C. then centrifuged at 14,000 rpm for 30 min at 4° C. to remove cell debris. 15 µL of 50% (w/v) protein NG or protein A beads (Santa Cruz Biotechnology) were added to 400 µL of supernatant and rotated for 30 min to preclear the samples. Samples were centrifuged at 14,000 rpm for 5 min, and the agarose pellet was discarded. Samples were split into two 200 µL aliquots and mixed with 25 µL of primary antibody conjugated to protein A or protein NG beads and rotated overnight at 4° C. Immunoprecipitates were collected by centrifugation at 7,000 rpm for 5 seconds, washed three times with wash buffer [300 mM NaCl, 50 mM Tris-HCl (pH 7.4), and 0.1% Triton X-100], and solubilized with of 10 µL elution buffer [100 mM Tris-HCl, 1% SDS, 10 mM DTT] and 5 µL of 4X NuPAGE LDS sample buffer (ThermoFisher Scientific). For western blots and immunoprecipitation experiments, the following primary antibodies were used: anti-HA (Roche, 11867423001), anti-FLAG (Sigma-Aldrich, F1804-200UG), anti-OPN3 (Santa Cruz Biotechnology, sc-98799), anti-MC1R (Santa Cruz Biotechnology, sc-6875), anti-MITF (ThermoFisher Scientific, MA514146), anti-TYR (Santa Cruz Biotechnology, sc-7833), anti-6-actin (ThermoFisher Scientific, MA515739) and anti-Integrin a5 (Santa Cruz Biotechnology, H-104). The primary antibodies were detected by incubation with goat anti-rat, goat anti-mouse or donkey anti-goat secondary antibodies coupled to HRP.

Immunofluorescence

Cells seeded on glass coverslips were fixed with 4% paraformaldehyde at room temperature for 10 min, incubated with blocking solution [0.2% saponin, 0.1% BSA, 0.02% sodium azide] for 1 hour, followed by overnight incubation with primary antibodies (1:200). For visualization, fluorescently labeled secondary antibodies (Life Technologies) (1:1000) were used. Micrographs were taken with a Zeiss LSM510 Meta confocal microscope. Image analysis was carried out using Zeiss Zen software and Image J software, as previously described by Dennis, et al.[14] Two proteins were considered completely colocalized if this ratio was higher than 50% and not colocalized if this ratio was lower than 10%.[15]

$Ca^{2+}$ Imaging and Light Stimulation

Cells cultured on glass coverslips were incubated for 20 min with 12 µM all-trans retinal (Sigma-Aldrich) in Ringer's solution [150 mM NaCl, 5 mM KCl, 1.8 mM $CaCl_2$, 1.2 mM $MgCl_2$, 10 mM HEPES, 10 mM D-glucose, pH 7.4], followed by wash and 20 min incubation with 7.5 µM Fluo4-AM (Life Technologies) and 250 µM sulfinpyrazone (uridine 5'-diphospho-glucuronosyltransferase inhibitor, Sigma-Aldrich) in Ringer's solution. Cells were washed with Ringer's solution and used for $Ca^{2+}$ imaging using an inverted microscope (Olympus IX71). Sequential images were acquired with a 20× objective every 2 sec before, during and after light stimulation: 200 mJ/cm² UVR ($\lambda_{max}$=360 nm); 200 mJ/cm² blue ($\lambda_{max}$=460 nm) or green ($\lambda_{max}$=560 nm) radiation was applied using a liquid guide coupled to a LED source (Prizmatix). Ionomycin (1 µM) was added at the end of each experiment to elicit a maximal $Ca^{2+}$ response, used for normalization. Changes in fluorescence intensity of individual cells as a function of time were obtained using MetaMorph software, then analyzed with MatLab and Microsoft Excel.

UVR was applied by using a 400 nm short pass and 280 nm long pass filters (Newport) attached to a 200 W Hg-Xe arc lamp (Newport) as previously described by Wicks NL et al.[16] For blue and green light, 460 and 560 nm LED light sources (Prizmatix) were used. For all experiments, cells were exposed to 20 mW/cm² radiation for 10 seconds, resulting in a total dose of 200 mJ/cm².

cAMP Imaging

The FRET-based genetically encoded cAMP indicator mTurq2Del-EPAC(dDEPCD)Q270E-tdcp173Venus(d) EPAC-$S^{H187}$ (Epac H187) was obtained from the Jalink Laboratory (Netherlands Cancer Institute). Cells were transfected with Epac H187 and ~24 hours after transfection cells were serum-starved in OPTI-MEM (ThermoFisher Scientific) for another ~24 hours. For PTX treatment, serum starved cells were incubated with 200 ng/mL PTX for 4 hours before the experiment. Coverslips were transferred to an imaging chamber with Ringer's solution. Sequential fluorescence images were acquired with MetaMorph software on an inverted microscope every 10 sec using CFP and FRET filter cubes: $\lambda_{ex}$=430 nm and CFP and YFP emissions were detected simultaneously using 470±20 nm and 530±25 nm band-pass filters. After acquiring 18 baseline images (3 min), 1 µM NDP-αMSH (Sigma-Aldrich) or 5 µM prostaglandin (Sigma-Aldrich) were added. After 54 images (9 min), a mix of 25 µM forskolin (FSK, Sigma-Aldrich) and 100 µM 3-isobutyl-1-methylxanthine (IBMX, Sigma-Aldrich) was added to elicit maximal cAMP response, used for normalization. Fluorescence emission intensities were quantified as F=FCFP/FYFP. Normalized fluorescence intensities were quantified using $F_{norm}(t)=(F_{cell}(t)-F_{min})/(F_{FSK+IBMX}-F_{min})$, where $F_{cell}$ is the fluorescence of an intracellular region of interest, FFSK+IBMX is the maximal fluorescence with FSK and IBMX, and $F_{min}$ is the baseline fluorescence before stimulation. Light-induced changes in fluorescence intensity were quantified using MetaMorph and Excel software (Microsoft). NDP-αMSH, prostaglandin, FSK and IBMX were solubilized in DMSO (Sigma-Aldrich) at >100× the final concentration, so that the final DMSO concentration in the imaging chamber remained <1% (v/v) for all experiments.

Melanin Assay

Confluent melanocytes cultured on 35 mm culture dishes were lysed and centrifuged at 14,000 rpm for 30 min at 4° C. to separate melanin from solubilized protein. Melanin pellets were solubilized with 1 M NaOH by incubation at 85° C. for a minimum of 1 hour. The volumes of the solubilized protein and solubilized melanin were noted. Spectrophotometric analysis of melanin content was determined by measuring absorbance at 405 nm and using a calibration curve obtained with synthetic melanin, as previously described.[17] Total melanin was determined as the product of the melanin concentration measured spectrophotometrically and the total volume of solubilized melanin. The protein content for each sample was measured using BCA protein assay kit (Pierce™, ThermoFisher Scientific). Total protein was determined as the product of the protein concentration measured with BCA and the volume of solubilized protein. Cellular melanin concentration was determined as total melanin/total protein for each condition; relative melanin content was calculated as the ratio of cellular melanin concentration for each experimental condition and control.

UV-Visible Spectroscopy

HEK293-GnTI-cells plated on 100 mm culture dishes were transfected, using calcium phosphate precipitation, with OPN3ΔC-c1D4 or OPN3(K299G)ΔC-c1D4 and harvested after three days in PBS, centrifuged at 3,500 rpm for 20 min and re-suspended in PBS. All subsequent steps of the protocol were performed in the dark. Cells were treated with 4.8 mM all-trans or 11-cis retinal at 4° C. for 30 min, lysed with 1% n-Dodecyl-β-D-maltoside (DDM, Sigma Aldrich) at 4° C. for 1 hour, then centrifuged at 3,500 rpm for 20 min. The supernatant containing the solubilized protein was incubated with pre-conjugated 1 D4 antibody-Sepharose beads at 4° C. for 2 h, then run through a disposable plastic column (ThermoFisher Scientific) and washed with 0.1% DDM. Proteins were eluted with 0.4 mM 1D4 peptide solution at 4° C. Absorbance spectra were measured on a Cary 50-UV visible spectrometer between 200 and 800 nm as previously described by Xie et al.[18] To test the presence of a Schiff-base bond between chromophore and K299 residue of OPN3, 0.8% SDS and 80 µM $NH_2OH$ were added to create retinal oxime, which absorbs maximally at 360 nm.[19]

Statistical Analysis

For each tested condition, at least three replicate experiments were performed, and the results were averaged. All data are given as means±SEM. Statistical differences among the experimental groups were analyzed by two-sided Student t-test when comparing two experimental groups. Significance was defined as *$p<0.05$ and **$p<0.01$.

Example 2

OPN3 is a Negative Regulator of MC1R-Mediated Signaling in Human Melanocytes

Basal melanin levels are regulated by MC1R, a Gαs-coupled receptor that signals by increasing cAMP levels in response to its endogenous agonist αMSH, ultimately leading to upregulation of the MITF and the main melanogenic enzyme TYR and resulting in increased cellular melanin. Because mosquito OPN3 is reportedly coupled to the Gαi/o subunit of G proteins, which signals by decreasing cellular cAMP levels, the effect of OPN3 on pigmentation was tested to determine if it could be due to its opposing effect on cAMP elevation via MC1R activation.

Figure 2:
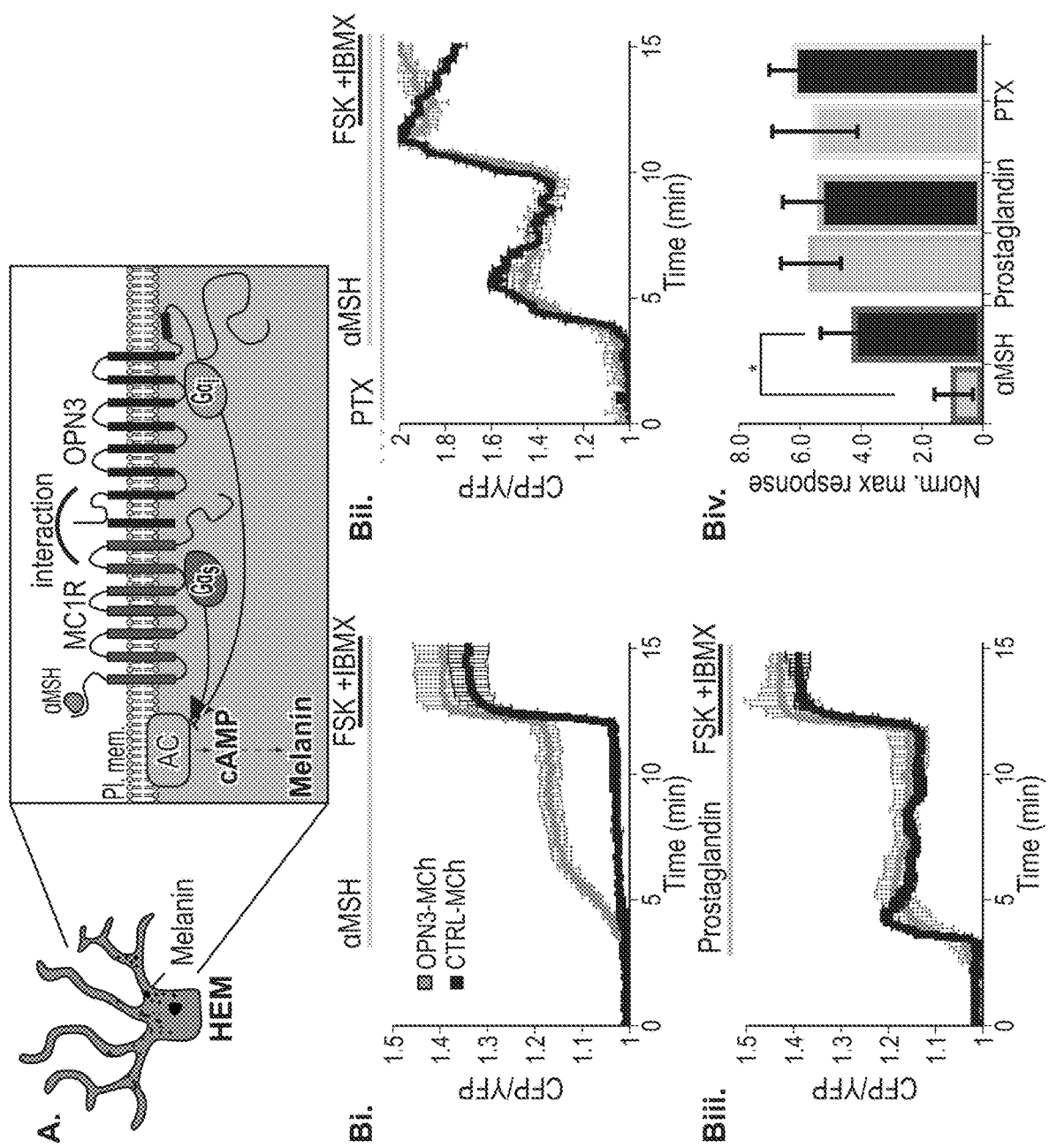
FIG. 2A-Bi-iv illustrates the OPN3 regulation of the MC1R-mediated melanogenic pathway.
FIG. 2Bi: MNT-1 melanocytes expressing OPN3-MCherry (OPN3-MCh) have a less robust cAMP response when stimulated with aMSH (MC1R agonist) than those expressing MCh.

To measure changes in cellular cAMP levels in response to MC1R activation, in the presence or absence of OPN3, a fluorescence resonance energy transfer (FRET)-based genetic cAMP sensor, Epac H187, was employed.[20] Epac H187 was first validated in MC1R transfected HeLa cells (data not shown), then transfected MNT-1 cells, which express endogenous MC1R, but low levels of OPN3 (data not shown), with Epac H187 and either OPN3-cMCh or MCh alone. Stimulation of control MCh-expressing MNT-1 cells with αMSH lead to a ~50% increase in cellular cAMP measured by the change in the Epac H187 FRET ratio (CFP/YFP), normalized to the maximum cAMP signal in these cells elicited by a mixture of the adenylyl cyclase activator forskolin (FSK) and phosphodiesterase inhibitor 3-isobutyl-1-methylxanthine (IBMX) (FIG. 2Bi and FIG. 2Biv). In contrast, MNT-1 cells expressing OPN3-MCh stimulated with αMSH under the same conditions, had a significantly smaller increase in cellular cAMP (~10%) normalized to the maximal cAMP signal (FIG. 2Bi and FIG. 2Biv), suggesting that OPN3 expression attenuates the MC1R-mediated cAMP signaling.

To determine whether OPN3 modulation of cAMP is specific to MC1R-mediated signaling, the endogenous prostaglandin EP2 receptor, which is also Gαs-coupled, was stimulated in MNT-1 cells expressing MCh or OPN3-cMCh. Stimulation of the EP2 receptor with 5 M prostaglandin in control (MCh) MNT-1 cells, led to a ~60% increase in cAMP measured by the change in the FRET ratio normalized to the maximal cAMP obtained with FSK+IBMX (FIG. 2Bii and FIG. 2Biv). Interestingly, EP2 receptor stimulation in MNT-1 cells expressing OPN3-cMCh at similar levels as in the previous experiment did not alter the amplitude of the prostaglandin-induce cAMP response (FIG. 2Bii and FIG. 2Biv), suggesting that OPN3 specifically modulates MC1R-mediated cAMP signaling.

OPN3 might regulate MC1R-mediated cAMP levels by activation of Gαi, which has the opposed effect on cellular cAMP levels, or by reducing the ability of MC1R to couple to Gαs and increase cAMP. To test if the effect of OPN3 on MC1R signaling requires Gαi coupling, MNT-1 cells expressing MCh or OPN3-cMCh were treated with Pertussis toxin (PTX) to inhibit Gαi signaling. PTX-treated MNT-1 cells expressing OPN3-cMCh have a robust cAMP response to αMSH, similar to PTX-treated control MNT-1 cells expressing MCh (FIG. 2Biii and FIG. 2Biv). This indicates that PTX-mediated inhibition of Gαi activation abolishes the effect of OPN3 on MC1R-signaling via cAMP and suggests that, in human melanocytes, OPN3 couples to Gαi to negatively modulate MC1R-mediated cAMP signaling (see FIG. 2A).

Example 3 OPN3 is Prevalent in the Hypothalamus where MC3R and MC4R are Located

OPN3 is a member of the light-sensitive opsin family (OPN1-OPN5) and has no known function in the hypothalamus despite being first discovered in this region in 1999. Its localization and function in the brain has yet to be characterized.

Figure 3:
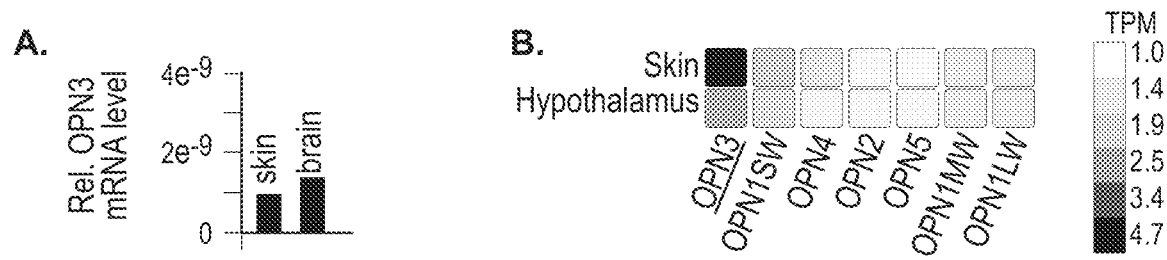
FIG. 3A-B shows that OPN3 is the most highly expressed opsin in the hypothalamus.

The levels of OPN3 mRNA were measured in human skin and brain tissue and compared. As shown in FIG. 3A, human OPN3 expression is nearly equivalent in the skin and in the brain. Expression of various human opsins was then measured in the hypothalamus and human skin and expressed in Transcripts per Kilobase Million (TPM) as sourced from GTEx. As illustrated in FIG. 3B, OPN3 was found to be the most highly expressed opsin in the hypothalamus.

The hypothalamus is a key site for the regulation of energy homeostasis, particularly in these sub-regions, PVN and ARC. Mapping of OPN3 across the brain in our novel OPN3-mCherry knock-in mouse model revealed its expression in a surprising number of regions associated with energy homeostasis, namely the paraventricular nucleus and arcuate nucleus of the hypothalamus.

MC3R, known to have a complex influence over energy homeostasis and appearing to have a collective anorexigenic effect, and MC4R, known to negatively regulate food intake and energy expenditure, are expressed in the same hypothalamic regions as OPN3. As illustrated in FIG. 1, the distribution of MC3R and MC4R was shown to have significant overlap with the distribution of OPN3 in the hypothalamus, particularly in the sub-regions, PVN and ARC.

Example 4

MC1R and MC4R/MC3R have High Sequence Conservation

Figure 12:
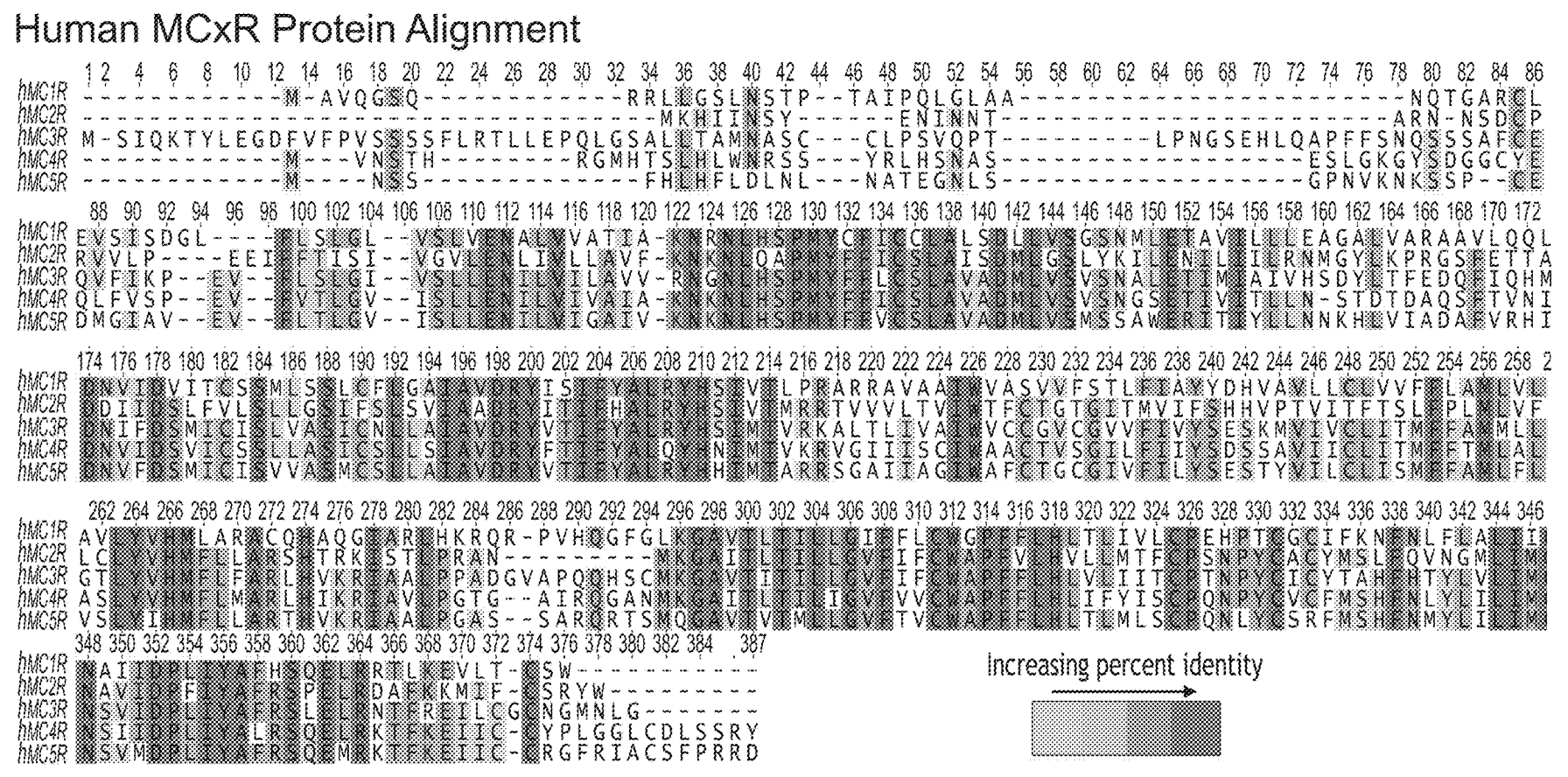

MC1R belongs to the same melanocortin receptor family (MCR) as neural MC3R and MC4R. The amino acid sequences obtained from the NCBI database[21] for human MC1R (NP_002377.4), MC2R (NP_001278840.1), MC3R (NP_063941.3), MC4R (NP_005903.2), and MC5R (NP_005904.1) were compared and the sequence identity was calculated by pBLAST alignments.[22] The sequence alignment is provided in FIG. 12.

Figure 4:
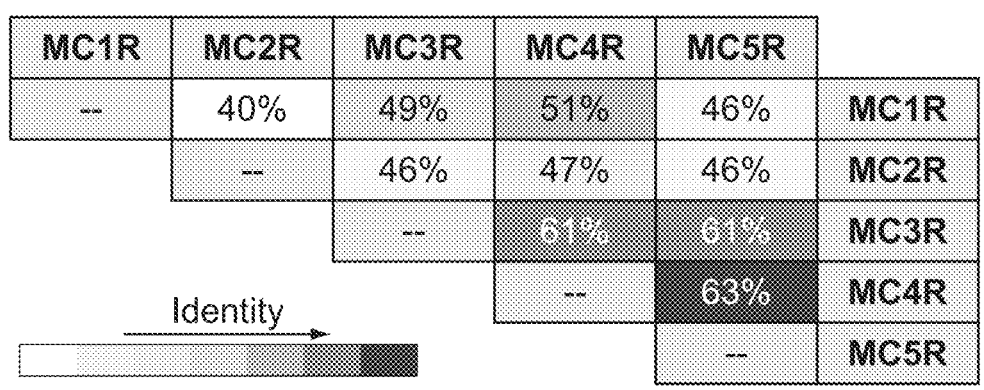
FIG. 4 provides percent identity between human MCR proteins and shows that MC1R and MC4R/MC3R have high sequence conservation, with MC4R having the highest sequence identity to MC1R. Identity was calculated by pBLAST alignments.

As summarized in FIG. 4, MC1R and MC4R/MC3R have high sequence conservation, with MC4R having the highest sequence identity to MC1R.

Example 5

OPN3 is Prevalent in the Hypothalamus where MC3R and MC4R are Located

The levels of OPN3 mRNA were measured in human skin and brain tissue and compared. As shown in FIG. 3A, human OPN3 expression is nearly equivalent in the skin and in the brain. Expression of various human opsins was then measured in the hypothalamus and human skin and expressed in Transcripts per Kilobase Million (TPM) as sourced from GTEx. As illustrated in FIG. 3B, OPN3 was found to be the most highly expressed opsin in the hypothalamus.

OPN3 is a member of the light-sensitive opsin family (OPN1-OPN5) and has no known function in the hypothalamus despite being first discovered in this region in 1999. OPN3 protein localization in the hypothalamus has not yet been characterized. Accordingly, OPN3 expression was investigated in the mouse hypothalamus with OPN3-mCherry mouse as immunostained with anti-mCherry.

The hypothalamus is a key site for the regulation of energy homeostasis, particularly in these sub-regions, PVN and ARC. Mapping of OPN3 across the brain in our novel OPN3-mCherry knock-in mouse model revealed its expression in a surprising number of regions associated with energy homeostasis, namely the paraventricular nucleus and arcuate nucleus of the hypothalamus.

Figure 6:
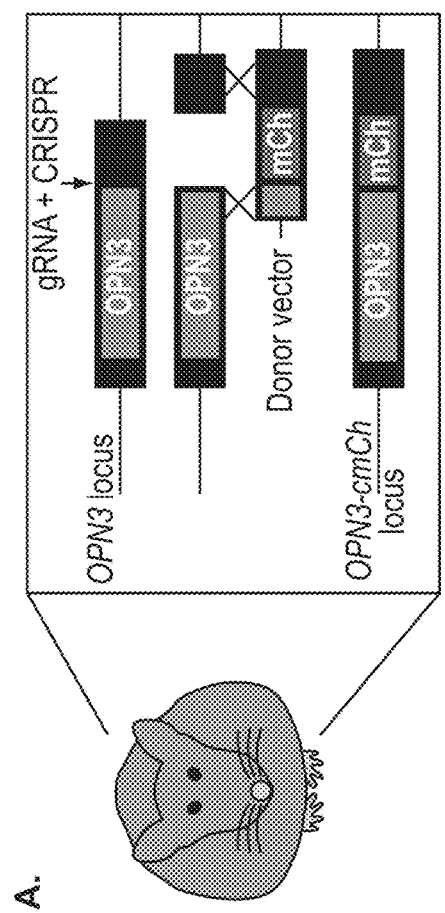
FIG. 6A-B shows the OPN3 expression in the mouse hypothalamus. OPN3 is expressed in the PVN and the ARC.
Figure 6:
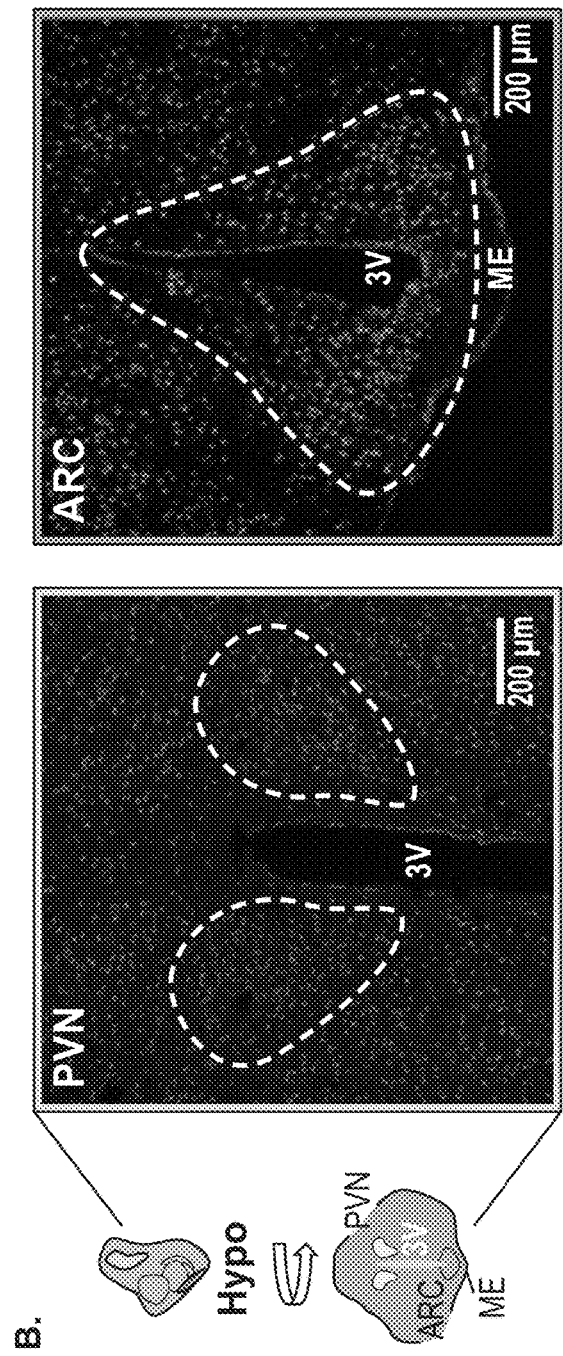

FIG. 6A provides schematic for the generation of an OPN3-mCherry mouse line which expresses OPN3-mCherry under the native OPN3 promoter. FIG. 6B shows OPN3 expression in the PVN and ARC. A more detailed study confirming these results was subsequently published by our laboratory.[23]

Figure 5:
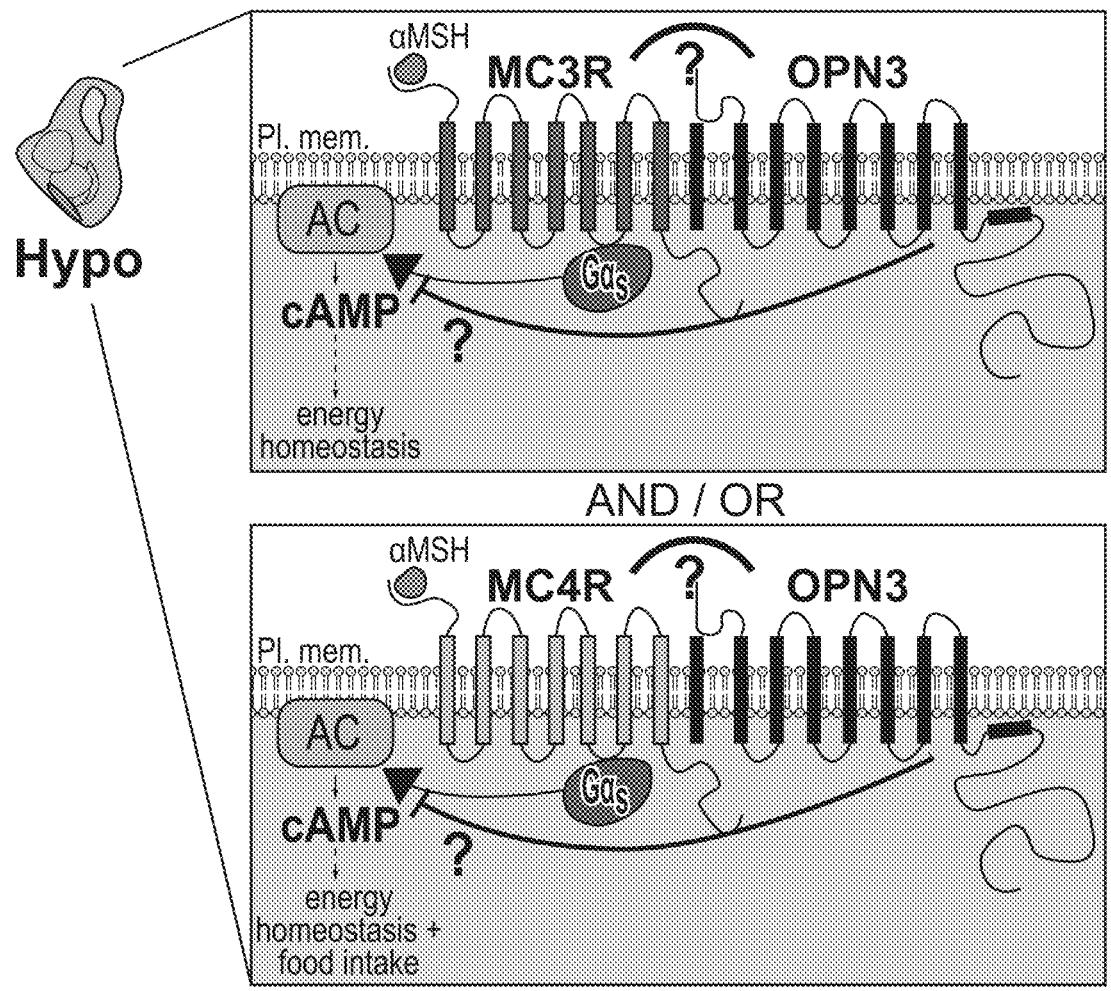
FIG. 5 depicts the mechanism of OPN3-mediated regulation of MC3R and/or MC4R in the hypothalamus. Abbreviations: AC: adenylyl cyclase; PI. mem: plasma membrane.
Figure 11:
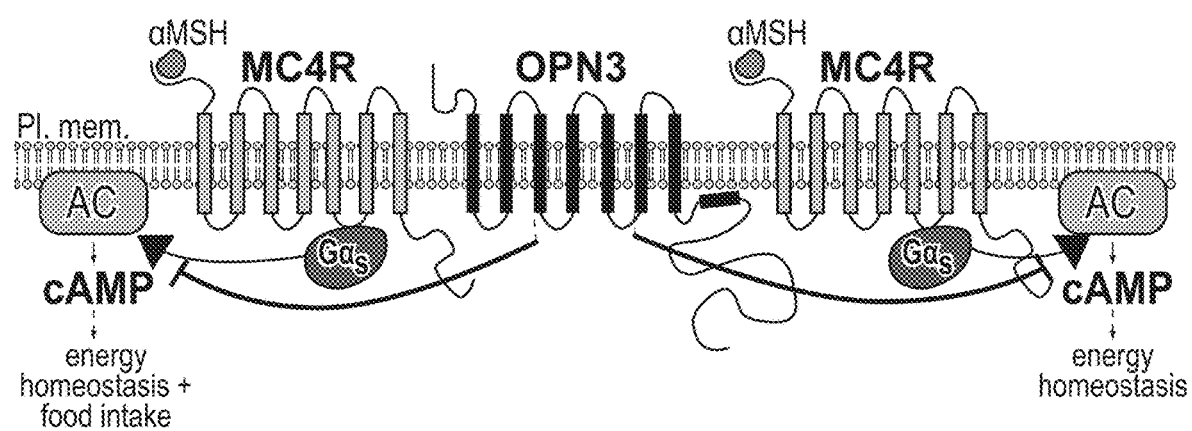
FIG. 11 provides a diagrammatic representation of the mechanism of OPN3-mediated regulation of MC3R and/or MC4R in the hypothalamus. Abbreviations: AC: adenylyl cyclase; PI. mem: plasma membrane.

It was hypothesized that, similar to OPN3 modulation of MC1R in skin, OPN3 functionally and physically interacts with MC3R and/or MC4R in the hypothalamus to negatively regulate cAMP signaling. FIG. 5 and FIG. 11 depict the proposed mechanism of OPN3-mediated regulation of MC3R and/or MC4R in the hypothalamus.

MC3R, known to have a complex influence over energy homeostasis and appearing to have a collective anorexigenic effect, and MC4R, known to negatively regulate food intake and energy expenditure, are expressed in the same hypothalamic regions as OPN3. As illustrated in FIG. 1, the distribution of MC3R and MC4R was shown to have significant overlap with the distribution of OPN3 in the hypothalamus, particularly in the sub-regions, PVN and ARC.

Example 6

OPN3 Forms a Complex with MC3R And MC4R

Example 1 provides evidence that OPN3 physically interacts with MC3R and MC4R in the skin. The present study investigated if OPN3 also interacts with MC3R and MC4R in the hypothalamus.

OPN3-cFLAG and MC3R-nHA or MC3R-nHA were co-expressed in HEK293T cells maintained under standard conditions in DMEM supplemented with 5% FBS and 100 units/ml penicillin/streptomycin and transiently transfected using Lipofectamine 2000. Cells plated on tissue culture dishes (100 mm) were rinsed with cold PBS before the addition of 500 μL lysis buffer [300 mM NaCl, 50 mM Tris-HCl (pH 7.4), 1% Triton X-100, and protease inhibitor mix (Roche)]. Cells were scraped and homogenized using a 22G syringe needle. Lysates were rotated end-over-end for 1 hour at 4° C. then centrifuged at 14,000 rpm for 30 min at 4° C. to remove cell debris. 15 μL of 50% (w/v) protein NG or protein A beads (Santa Cruz Biotechnology) were added to 400 μL of supernatant and rotated for 30 min to preclear the samples. Samples were centrifuged at 14,000 rpm for 5 min, and the agarose pellet was discarded. Samples were split into two 200 μL aliquots and mixed with 25 μL of primary antibody conjugated to protein A or protein NG beads and rotated overnight at 4° C. Immunoprecipitates were collected by centrifugation at 7,000 rpm for 5 s, washed three times with wash buffer [300 mM NaCl, 50 mM Tris-HCl (pH 7.4), and 0.1% Triton X-100], and solubilized with of 10 μL elution buffer [100 mM Tris-HCl, 1% SDS, 10 mM DTT] and 5 μl of 4X NuPAGE LDS sample buffer (ThermoFisher Scientific).

Figure 7:
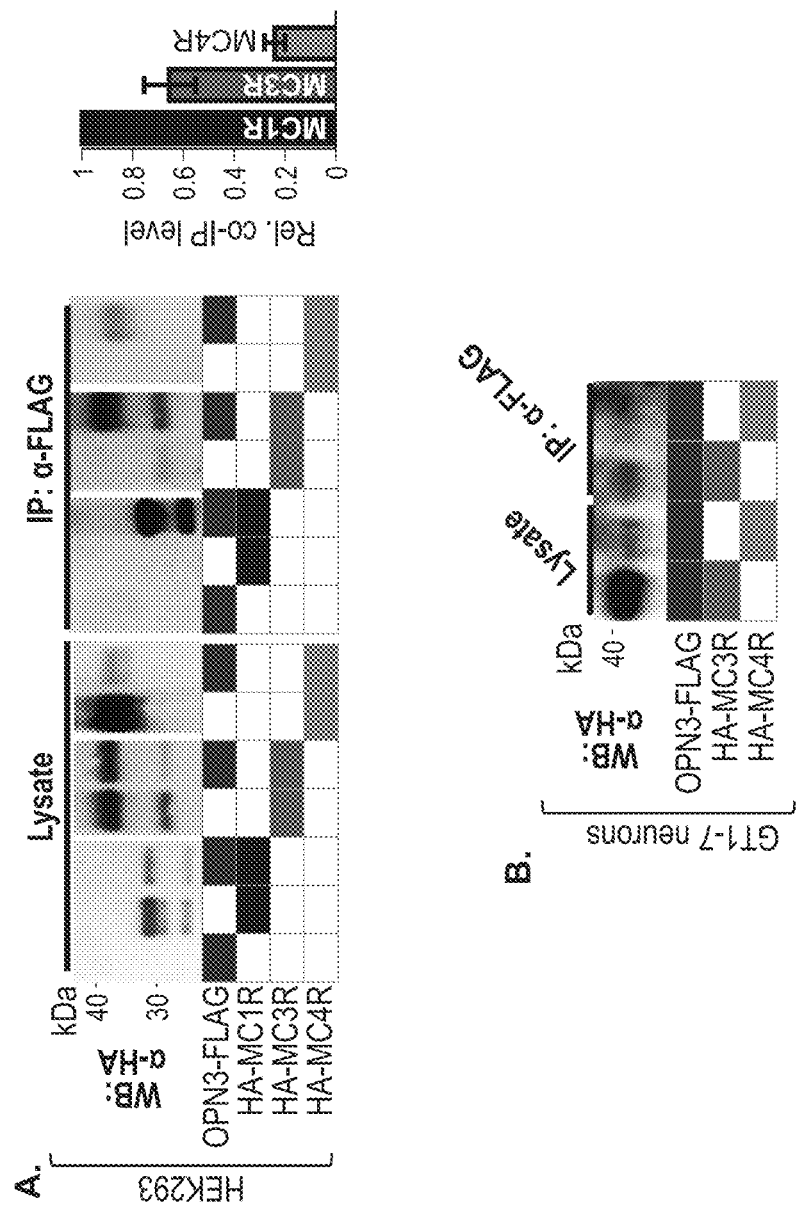
FIG. 7A-B shows that OPN3 forms a complex with MC3R. OPN3 interacts with MC3R, and to a lesser extent, MC4R.

As shown in FIG. 7, OPN3 interacts and forms a complex with MC3R, and to a lesser extent, MC4R. FIG. 7A provides the coimmunoprecipitation of HEK293 cells expressing the indicated OPN3, MC1R, MC3R, or MC4R constructs.

Importantly, immunoprecipitating OPN3-FLAG expressed in GT1-7 neuronal hypothalamic cells followed by immunoblotting with an anti-HA antibodies revealed that OPN3 and MC3R and to a lesser extent OPN3 and MC4R also form a complex in GT1-7 hypothalamic neuronal cells (FIG. 7B).

Example 7

OPN3 Modulates MC3R—and MC4R-Mediated Signaling in Hypothalamic Cells

The present study investigated if OPN3 modulates MC3R—and MC4R-mediated signaling in hypothalamic mHypoE-39 neurons.

Figure 8:
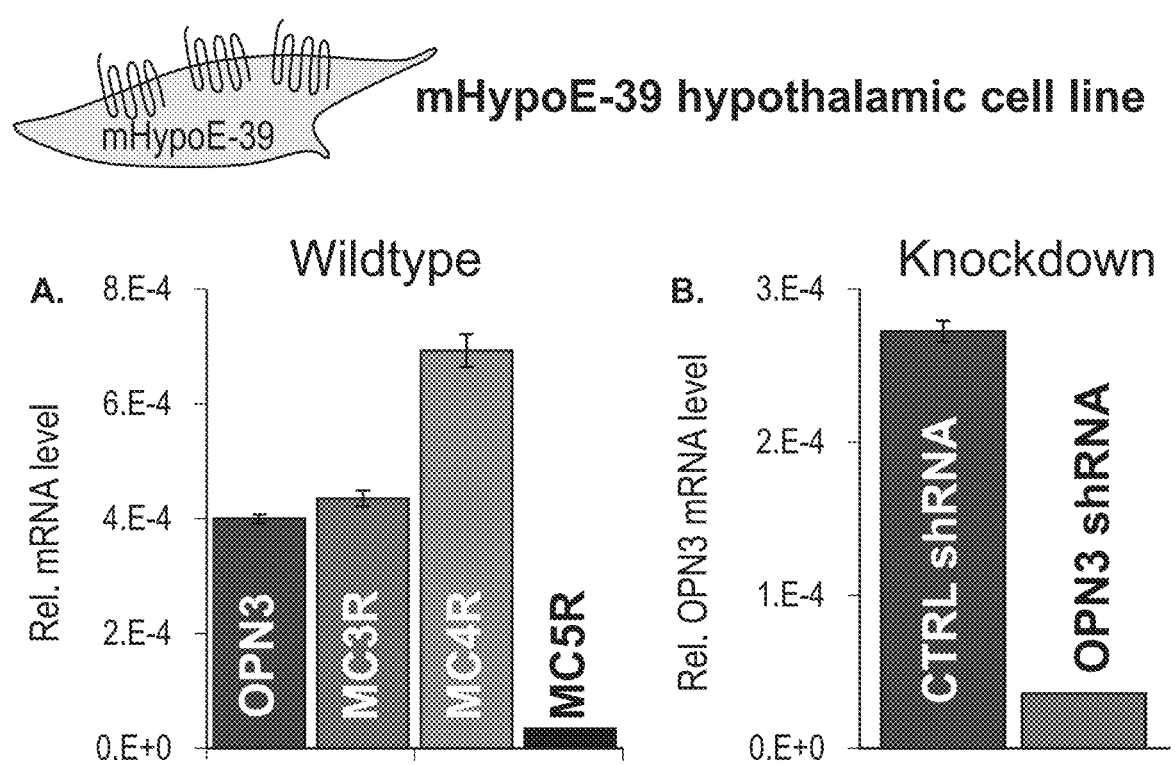
FIG. 8A-B shows that OPN3, MC3R and MC4R are expressed in mHypoE-39 neurons.
FIG. 8C: Quantification of the maximal cAMP responses in A (purple outline) and B (green outline). n=5-7 cells over two independent experiments. Error bars±SEM.

As shown in FIG. 8, OPN3, MC3R and MC4R are all expressed in mHypoE-39 neurons. FIG. 8A provides the relative mRNA expression levels of indicated genes, namely, OPN3, MC3R, MC4R, and MCSR. 3 μg of total RNA was extracted from the mHypo-39 hypothalamic cell lines using the RNeasy Plus Kit (Qiagen) and reverse transcribed (RT) using SuperScript III kit (Life Technologies). The resulting cDNA was used as template for qPCR reactions using primers specific for OPN3, MC3R, MC4R or MCSR. Reactions were prepared according to the manufacturer's protocol using SYBR Select Master Mix (Invitrogen) and cycled on a VIIA-7 Real-Time PCR System (Applied Biosystems).

β-actin was used as an internal control and all reactions were run in triplicate. mRNA levels were quantified by calculating average $2^{-\Delta Ct}$ values, where Ct is the cycle number for the control and target transcript at the chosen threshold. $\Delta Ct=Ct_{target}-Ct_{\beta\text{-}actin}$ was calculated by subtracting the average Ct of β-actin from the average Ct of the target transcript. Primers were designed to span an exon-exon junction to avoid amplification of any contaminate genomic DNA using Primer3.[24]

OPN3 mRNA levels were also assessed in mHypoE-39 with shRNA-mediated knockdown of OPN3. The shRNAs used in this study were three commercially-available OPN3 shRNAs (Sigma-Aldrich). The details and sequences of the three shRNAs are provided in Table 1.

TABLE 1

| shRNA Sequences | |
|---|---|
| TRCN0000028389 Product Details | Region: CDS    Mean KnockDown<br>TRC Version: 1   Level: 0.75<br>                Cell Line: NIH/3T3<br>                Clone ID:<br>                NM_010098.1-1218s1c1<br>Sequence: CCGGCGCATCTAAGGTCGATGT<br>CATCTCGAGATGACATCGACCTTAGATGCGTT<br>TTT<br>SEQ ID NO: 1 |
| TRCN0000028313 Product Details | Region: CDS    Mean KnockDown<br>TRC Version: 1   Level: 0.77<br>                Cell Line: NIH/3T3<br>                Clone ID:<br>                NM_010098.1-519s1c1<br>Sequence: CCGGCATTACCTATATATGGCT<br>CTACTCGAGTAGAGCGAGATATAGGTAATGTT<br>TTT<br>SEQ ID NO: 2 |
| TRCN0000028305 Product Details | Region: 3UTR    Mean KnockDown<br>TRC Version: 1   Level: 0.71<br>                Cell Line: NIH/3T3<br>                Clone ID:<br>                NM_010098.1-1402s1c1<br>Sequence: CCGGCGACTGAGCAAGAGAAAT<br>TATCTCGAGATAATTTSTGTTGCTCAGTGGTT<br>TTT<br>SEQ ID NO: 3 |

For these experiments, mHypo-39 cells were transduced with either OPN3-targeted or scrambled shRNAs using BLOCK-IT™ Lentiviral RNAi expression system according to manufacturers' instructions. The mHypo-39 cells expressing the OPN3shRNA were selected using blasticidin treatment. A shown in FIG. 8B, cells expressing OPN3-targeted shRNA cells had less than 12% of the levels in control shRNA cells.

To test if OPN3 modulates MC3R or MC4R signaling, the amplitude of the cAMP responses evoked by activation of the receptors were quantified. Epac-H187, a genetic FRET-based cAMP indicator were used for intracellular cAMP imaging. Cells were transfected with Epac-H187 two days prior to experimentation; one day prior, cells were serum-starved in OPTI-MEM. PTX treatment was used to test the Gai-dependence of the modulation. Cells were incubated in 200 ng/ml PTX for 4 hours before the experiment. Coverslips were transferred to an imaging chamber and covered with 1 ml Ringers' solution [150 mM NaCl, 5 mM KCl, 1.8 mM CaCl$_2$, 1.2 mM MgCl$_2$, 10 mM HEPES, 10 mM D-glucose]. Time-lapse fluorescence images were acquired every 10 s using CFP and FRET light cubes on our inverted microscope controlled with MetaMorph software. Cells were exposed to an excitation wavelength of 430 nm and both CFP and YFP emissions were detected simultaneously through 470±20 nm and 530±25 nm band-pass filters. After acquiring 18 baseline images (3 min), 1 µM NDP-αMSH (Sigma-Aldrich) was added to the surrounding Ringers' solution. After acquiring 54 images (9 min), a mixture of 25 µM forskolin (Sigma-Aldrich) and 100 µM IBMX (3-isobutyl-1-methylxanthine, Sigma-Aldrich) was added to elicit maximal cAMP response, used for normalization. Fluorescence intensities were quantified as $F=f_{CFP}/f_{YFP}$ (where f is emission intensity). Normalized fluorescence intensities were quantified using $F_{norm(t)}=(F_{cell(t)}-F_{min})/(F_{FSK+IBMX}-F_{min})$ [$F_{cell}$ is the fluorescence of an intracellular region of interest, $F_{FSK+IBMX}$ is the maximal fluorescence with FSK and IBMX, and $F_{min}$ is the baseline fluorescence before stimulation]. For each tested condition and standard, three replicate experiments were performed, and results were averaged.

Figure 9:
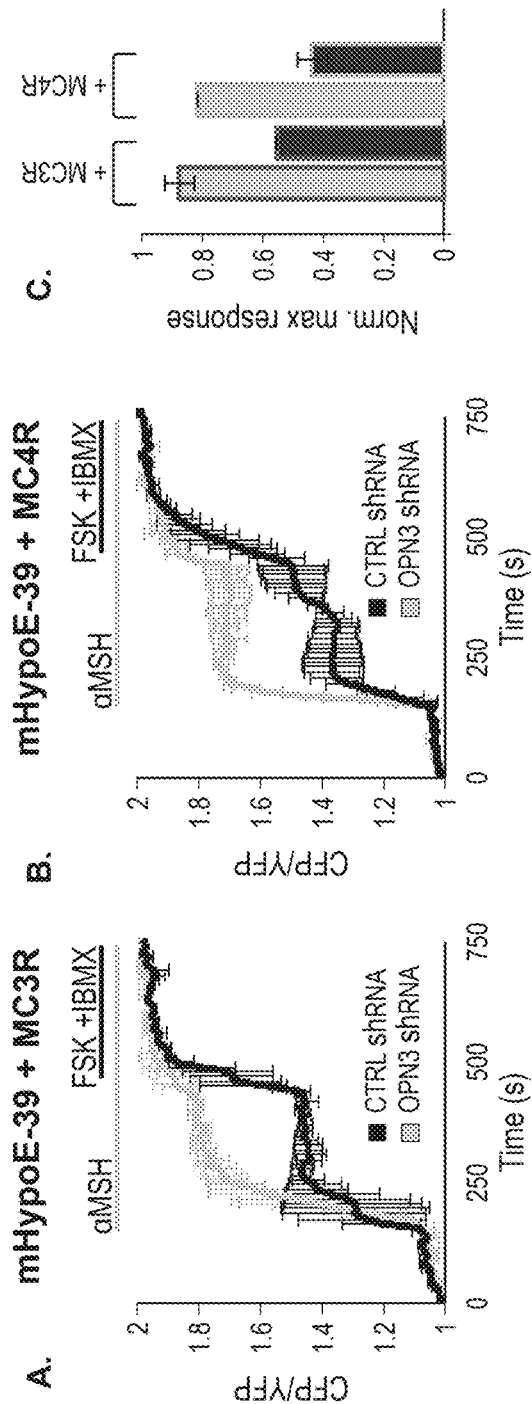
FIG. 9A-C illustrates that OPN3 negatively regulates aMSH-induced cAMP signaling in mHypoE-39.

FIG. 9 illustrates that OPN3 negatively regulates αMSH-induced cAMP signaling in mHypoE-39. mHypoE-39 cells expressing control scrambled shRNA (CTRL shRNA) or OPN3-targetted shRNA (OPN3 shRNA) were transfected with MC3R-n(HAx3) and EPACH187. As shown in FIG. 9A, the cells with reduced levels of OPN3 (grey) had a larger cAMP response to αMSH compared to CTRL (blue).

mHypoE-39 cells expressing control scrambled shRNA (CTRL shRNA) or OPN3-targetted shRNA (OPN3 shRNA) were transfected with MC4R-n(HAx3) and EPACH187. As shown in FIG. 9B, the cells with reduced levels of OPN3 (grey) have a larger cAMP response to αMSH compared to CTRL (blue). FIG. 9C provides a bar graph showing the quantification of the maximal cAMP responses in A (purple outline) and B (green outline). These data suggest OPN3 negatively regulates αMSH-induced cAMP signaling of both MC3R and MC4R.

Example 8

In Vivo Assessment of OPN3 Downregulation in MC3R—and MC4R-Based Metabolic Diseases The present study assessed the OPN3 downregulation on the physiological or pathological function of different organs using a mouse model that does not express OPN3 (OPN3$^{-/-}$).

Figure 10:
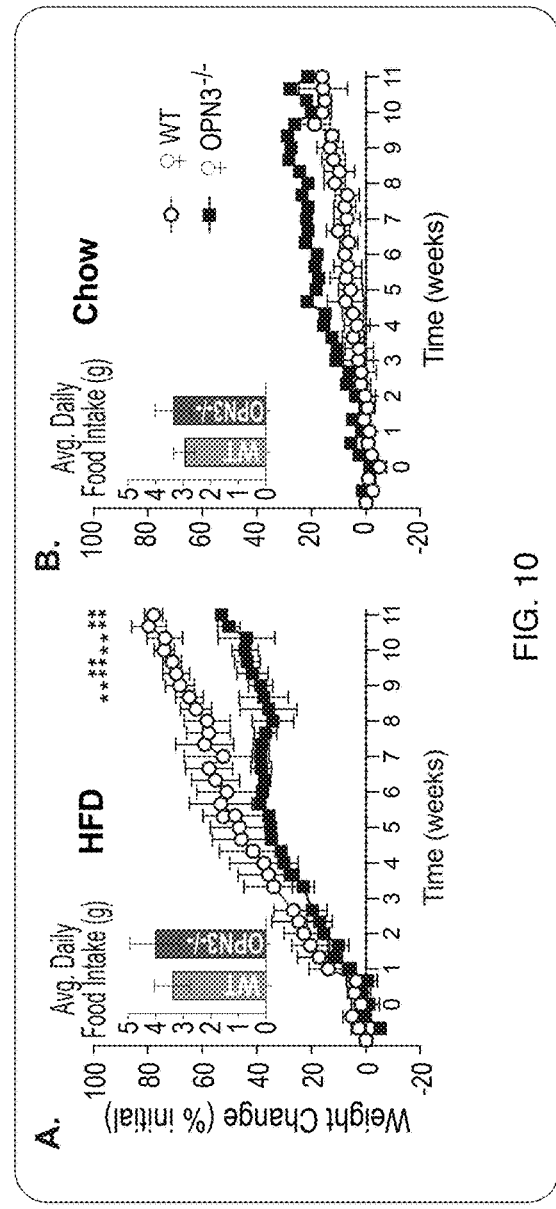
FIG. 10A-B shows that OPN3$^{-/-}$ female mice have lower high fat diet-induced weight gain.

We tested if OPN3 regulates metabolic function by modulating MC3R or MC4R activity by exposing OPN3$^{-/-}$ and wild-type to high-fat diet, a known model for inducing obesity. OPN3$^{-/-}$ or wildtype (WT) mice (all female) were subjected to either a regular diet (Chow) or high fat diet (HFD) for 12 weeks. The food intake and body weight were measured regularly. As illustrated in FIG. 10, OPN3$^{-/-}$ female mice had lower high fat diet-induced weight gain than wild-type female mice. When fed a high fat diet (HFD) for 11 weeks, WT mice (n=2) had a significant increase in mean body weight compared to OPN3$^{-/-}$ female mice (n=2), p<0.0001 (FIG. 10A). In contrast, when fed a regular chow diet for 11 weeks, there was no significant differences in mean body weight compared between female WT (n=2) and OPN3$^{-/-}$ (n=1) mice (FIG. 10B). Importantly, there was no significant differences in the average food intake of OPN3$^{-/-}$ and WT mice on each diet, p>0.05.

Therefore, OPN3$^{-/-}$ mice gained significantly less weight compared to the control wild type mice when fed a high fat diet, while consuming the same amount of food/calories. These in vivo data suggests that OPN3 downregulation may provide an effective therapy for the treatment of MC3R—and MC4R-based obesity and obesity-related metabolic disorders.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize or be able to ascertain using no more than routine experimentation, many equivalents to the specific embodiments described herein. Such equivalents are intended to be encompassed by the following claims.

REFERENCES

[1] See, e.g., Isselbacher et al. (1996). HARRISON'S PRINCIPLES OF INTERNAL MEDICINE, 13 ed., 1814-1882.
[2] THE MERCK MANUAL OF DIAGNOSIS AND THERAPY, 19th Edition, published by Merck Sharp & Dohme Corp., 2011 (ISBN 978-0-911910-19-3).
[3] THE ENCYCLOPEDIA OF MOLECULAR CELL BIOLOGY AND MOLECULAR MEDICINE, Robert S. Porter et al. (eds.), published by Blackwell Science Ltd., 1999-2012 (ISBN 9783527600908).
[4] MOLECULAR BIOLOGY AND BIOTECHNOLOGY: A COMPREHENSIVE DESK REFERENCE, Robert A. Meyers (ed.), published by VCH Publishers, Inc., 1995 (ISBN 1-56081-569-8).
[5] IMMUNOLOGY by Werner Luttmann, published by Elsevier, 2006.
[6] JANEWAY'S IMMUNOBIOLOGY, Kenneth Murphy, Allan Mowat, Casey Weaver (eds.), Taylor & Francis Limited, 2014 (ISBN 0815345305, 9780815345305).
[7] LEWIN'S GENES XI, published by Jones & Bartlett Publishers, 2014 (ISBN-1449659055).
[8] MOLECULAR CLONING: A LABORATORY MANUAL, 4$^{th}$ edn., Green M R and Sambrook J (eds.), Cold Spring Harbor Laboratory Press, Cold Spring Harbor, N.Y., USA (2012) (ISBN 1936113414).
[9] BASIC METHODS IN MOLECULAR BIOLOGY, Davis et al. (eds.), Elsevier Science Publishing, Inc., New York, USA (2012) (ISBN 044460149X).
[10] LABORATORY METHODS IN ENZYMOLOGY: DNA, Jon Lorsch (ed.) Elsevier, 2013 (ISBN 0124199542).
[11] CURRENT PROTOCOLS IN MOLECULAR BIOLOGY (CPMB), Frederick M. Ausubel (ed.), John Wiley and Sons, 2014 (ISBN 047150338X, 9780471503385).
[12] CURRENT PROTOCOLS IN PROTEIN SCIENCE (CPPS), John E. Coligan (ed.), John Wiley and Sons, Inc., 2005.
[13] CURRENT PROTOCOLS IN IMMUNOLOGY (CPI), Coligan J E, Kruisbeek A, Margulies D H, Shevach E H, and Strobe W, (eds.) John Wiley and Sons, Inc., 2003 (ISBN 0471142735, 9780471142737).
[14] Dennis M K, et al. (2016). "BLOC-1 and BLOC-3 regulate VAMP7 cycling to and from melanosomes via distinct tubular transport carriers." J Cell Biol 214:293-308.

[15] Li Q, et al. (2004). "A syntaxin 1, Galpha(o), and N-type calcium channel complex at a presynaptic nerve terminal: analysis by quantitative immunocolocalization." J Neurosci 24:4070-4081.

[16] Wicks N L et al. (2011). "UVA phototransduction drives early melanin synthesis in human melanocytes." Curr Biol 21:1906-1911.

[17] Wicks N L et al. (2011). Id.

[18] Xie G, Gross A K, Oprian D D (2003). "An opsin mutant with increased thermal stability." Biochemistry 42: 1995-2001.

[19] Sieving P A, et al. (2001). "Constitutive "light" adaptation in rods from G9OD rhodopsin: a mechanism for human congenital nightblindness without rod cell loss." J Neurosci 21: 5449-5460.

[20] Klarenbeek J. et al. (2015). "Fourth-generation epac-based FRET sensors for cAMP feature exceptional brightness, photostability and dynamic range: characterization of dedicated sensors for FLIM, for ratiometry and with high affinity." PLoS ONE 10:e0122513.

[21] https://www.ncbi.nlm.nih.gov/protein

[22] https://blast.ncbi.nlm.nih.gov/Blast.cgi?PAGE=Proteins

[23] Olinski L E, Tsuda A C, Kauer J A, and Oancea E. (2020). "Endogenous Opsin 3 (OPN3) Protein Expression in the Adult Brain Using a Novel OPN3-mCherry Knock-In Mouse Model." 7(5) eNeuro.0107-20.2020 1-19.

[24] http://bioinfo.ut.ee/primer3-0.4.0/

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of treating obesity or an obesity-related disorder comprising the step of administering to a subject in need thereof a composition that downregulates opsin 3 (OPN3) protein expression, OPN3 gene expression, and/or OPN3 activation, wherein the composition comprises an OPN3-targeted shRNA selected from the group consisting of: SEQ ID NO: 1, SEQ ID NO: 2, SEQ ID NO: 3, and a combination thereof.

2. The method of claim 1, wherein the opsin 3 (OPN3) protein expression, OPN3 gene expression, and/or OPN3 activation is downregulated in the hypothalamus of the subject.

3. The method of claim 1, wherein the downregulation of OPN3 protein expression, OPN3 gene expression, and/or OPN3 activation results in an upregulation of Melanocortin-3 receptor (MC3R) signaling and Melanocortin-4 receptor (MC4R) signaling.

4. The method of claim 1, wherein the obesity-related disorder is selected from the group consisting of: glucose intolerance, diabetes and metabolic syndrome.

* * * * *